United States Patent
Holyoke, Jr.

(10) Patent No.: US 11,044,910 B2
(45) Date of Patent: Jun. 29, 2021

(54) MESOIONIC INSECTICIDES

(71) Applicant: FMC Corporation, Philadelphia, PA (US)

(72) Inventor: Caleb William Holyoke, Jr., Newark, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 16/612,097

(22) PCT Filed: May 4, 2018

(86) PCT No.: PCT/US2018/031097
§ 371 (c)(1),
(2) Date: Nov. 8, 2019

(87) PCT Pub. No.: WO2018/208595
PCT Pub. Date: Nov. 15, 2018

(65) Prior Publication Data
US 2020/0093133 A1     Mar. 26, 2020

Related U.S. Application Data

(60) Provisional application No. 62/503,369, filed on May 9, 2017, provisional application No. 62/548,489, filed on Aug. 22, 2017.

(51) Int. Cl.
*A01N 43/90* (2006.01)
*C07D 471/04* (2006.01)

(52) U.S. Cl.
CPC .......... *A01N 43/90* (2013.01); *C07D 471/04* (2013.01)

(58) Field of Classification Search
CPC ............................ A01N 43/90; C07D 471/04
USPC ........................................................ 514/300
See application file for complete search history.

(56) References Cited

U.S. PATENT DOCUMENTS

| | | | | |
|---|---|---|---|---|
| 8,552,007 B2 * | 10/2013 | Holyoke, Jr. | ........... | A01N 43/90 514/259.4 |
| 8,697,707 B2 * | 4/2014 | Holyoke, Jr. | ........... | A61P 33/00 514/259.41 |
| 8,722,690 B2 * | 5/2014 | Zhang | ..................... | A61P 43/00 514/259.41 |
| 9,018,220 B2 * | 4/2015 | Holyoke, Jr. | ........ | C07D 471/04 514/259.4 |
| 9,210,932 B2 * | 12/2015 | Zhang | ..................... | A61P 43/00 |
| 9,314,025 B2 * | 4/2016 | Holyoke, Jr. | ........... | A01N 43/90 |
| 9,596,856 B2 * | 3/2017 | Zhang | ..................... | A61P 33/00 |
| 2010/0323887 A1 * | 12/2010 | Holyoke, Jr. | ........ | C07D 401/06 504/100 |
| 2012/0115722 A1 * | 5/2012 | Holyoke, Jr. | ........... | A01N 43/90 504/100 |
| 2012/0122679 A1 * | 5/2012 | Zhang | ................... | C07D 513/04 504/100 |
| 2012/0122680 A1 * | 5/2012 | Holyoke, Jr. | ........ | C07D 498/04 504/100 |
| 2012/0277100 A1 * | 11/2012 | Zhang | ................... | C07D 417/06 504/100 |
| 2013/0338002 A1 * | 12/2013 | Holyoke, Jr. | ........ | C07D 513/04 504/100 |
| 2014/0187776 A1 * | 7/2014 | Holyoke, Jr. | .......... | A01N 43/90 544/282 |
| 2014/0206536 A1 * | 7/2014 | Zhang | ..................... | A01N 43/54 504/100 |
| 2016/0066577 A1 * | 3/2016 | Zhang | ..................... | A61P 33/14 504/100 |
| 2018/0282323 A1 * | 10/2018 | Heil | ........................ | A61P 33/00 |
| 2020/0037600 A1 * | 2/2020 | Hoffmeister | ............ | A61P 33/14 |

FOREIGN PATENT DOCUMENTS

| | | | | |
|---|---|---|---|---|
| EP | 3636644 A1 * | 4/2020 | .......... | C07D 213/74 |
| WO | 20110017347 | 2/2011 | | |
| WO | 201200106495 | 8/2012 | | |
| WO | WO-2017093214 A1 * | 6/2017 | .......... | C07D 487/04 |
| WO | WO-2018108730 A1 * | 6/2018 | .......... | C07D 471/04 |
| WO | WO-2018189077 A1 * | 10/2018 | ............ | A01M 25/00 |
| WO | WO-2018229202 A1 * | 12/2018 | ............. | A01N 43/50 |
| WO | WO-2019086474 A1 * | 5/2019 | .......... | C07D 471/04 |

OTHER PUBLICATIONS

Edstrom; J. Org. Chem. 1994, 59, 9, 2473-2481. (Year: 1994).*
Lawson; J. Chem. Soc., 1959, 2865-2871. (Year: 1959).*
Zhang et al., "Mesoionic pyrido[1,2-a]pyrimidinones: A novel class of insecticides inhibiting nicotinic acetylocholine receptors", Bioorganic & Medicinal Chemistry Letters, vol. 26, No. 22, 2016, pp. 5444-5449 (XP029803192).
Zhang et al., "Mesoionic pyrido[1,2-a]pyrimidinones: Discovery of triflumezopyrim as a potent hopper insecticide", Bioorganic & Medicinal Chemistry Letters, vol. 27, No. 1, 2016, pp. 16-20 (XP029837682).

(Continued)

*Primary Examiner* — Daniel R Carcanague
(74) *Attorney, Agent, or Firm* — FMC Corporation; Sabine U Epelbaum

(57) ABSTRACT

Disclosed are compounds of Formula 1, including all geometric and stereoisomers, N-oxides, and salts thereof,

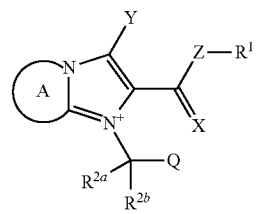

wherein A, X, Y, Z, $R^1$, $R^{2a}$, $R^{2b}$ and Q are as defined in the disclosure. Also disclosed are compositions containing the compounds of Formula 1 and methods for controlling an invertebrate pest comprising contacting the invertebrate pest or its environment with a biologically effective amount of a compound or a composition of the invention.

10 Claims, No Drawings

(56) References Cited

OTHER PUBLICATIONS

Zhang et al., "Mesoionic pyrido[1,2-a]pyrimidinones: Discovery of dicloromezotiaz as a lepidoptera insecticide acting on nicotinic acetylcholine receptors", Bioorganic & Medicinal Chemistry Letters, vol. 27, No. 4, Jan. 5, 2017, pp. 911-917 (XP029906421).
International Search Report of corresponding PCT/US2018/031097 dated Aug. 27, 2018.

* cited by examiner

MESOIONIC INSECTICIDES

CROSS-REFERENCE TO RELATED APPLICATIONS

This application is a national stage application, filed under 35 U.S.C. § 371, of International Patent Application No. PCT/US2018/031097, filed May 4, 2018, which claims the benefit of U.S. Provisional Application Nos. 62/503,369, filed May 9, 2017, and 62/548,489, filed Aug. 22, 2017, all of which are incorporated by reference herein in their entirety.

FIELD OF THE INVENTION

This invention relates to certain mesoionic compounds, their N-oxides, salts and compositions suitable for agronomic and nonagronomic uses, and methods of their use for controlling invertebrate pests such as arthropods in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public and animal health is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all geometric and stereoisomers), N-oxides, and salts thereof, and compositions containing them and their use for controlling invertebrate pests:

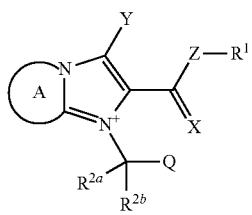

1 wherein
X is O or S;
Y is O or S;
A is a 5-, 6- or 7-membered ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and the sulfur atom ring members are independently selected from $S(=O)_n$, each ring unsubstituted or substituted with up to 3 substituents independently selected from $R^3$;

Z is a direct bond; or a 1- to 4-atom chain containing chain members selected from carbon atoms and up to 2 heteroatoms independently selected from up to 2 O, up to 2 S, and up to 2 N, wherein up to 2 carbon atom chain members are independently selected from $C(=O)$ and $C(=S)$ and the sulfur atom chain members are independently selected from $S(=O)_n$, each 1- to 4-atom chain being unsubstituted or substituted with up to 4 substituents independently selected from $R^5$, or substituted with up to 9 halogen when $R^5$ is halogen;

$R^1$ is 1H or halogen; a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u$ ($=NR^{19})_z$, each ring or ring system unsubstituted or substituted with up to 8 substituents independently selected from $R^4$; provided that when Z is a direct bond, $R^1$ is other than H or halogen;

$R^{2a}$ and $R^{2b}$ are independently H, halogen, cyano, $C_1$-$C_3$ alkyl, $C_2$-$C_3$ alkenyl or $C_2$-$C_3$ alkynyl; or $R^{2a}$ and $R^{21b}$ are taken together to form a 3- to 6-membered ring containing ring members selected from carbon atoms and up to one heteroatom selected from O, N and $S(O)_n$;

Q is a 5- or 6-membered heteroaromatic ring, unsubstituted or substituted with up to 3 substituents independently selected from $R^6$;

each $R^3$ is independently halogen, cyano, hydroxy, amino, nitro, $C(=O)OH$, $C(=O)NH_2$, $SO_2NH_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl or $C_2$-$C_6$ haloalkylcarbonyl;

each $R^4$ is independently halogen, cyano, hydroxy, amino, nitro, $SF_5$, OCN, SCN, CHO, $C(=O)OH$, $C(=O)NH_2$, $C(=S)NH_2$, $SO_2NH_2$, $C(=O)R^{13}$, $C(=O)OR^{13}$, $NHR^{13}$, $NR^{13}R^{14}$, $C(=O)NR^{16}R^{14}$, $C(=S)NR^{16}R^{14}$, $SO_2NR^{16}R^{14}$, $OC(=O)R^{16}$, $OC(=O)OR^{13}$, $OC(=O)NR^{16}R^{14}$, $N(R^{16})C(=O)R^{16}$, $N(R^{16})C(=O)OR^{14}$, $N(R^{16})C(=O)NR^{16}R^{17}$, $OSO_2R^{13}$, $OSO_2NR^{16}R^{17}$, $NR^{16}SO_2R^{13}$, $NR^{16}SO_2NR^{16}R^{17}$, $Si(R^{13}R^{14}R^{15})$, $C(=NR^{16})R^{17}$, $C(=NOR^{16})R^{17}$, $C(=NNR^{16}R^{17})R^{18}$, $C(=NN(C(=O)R^{14})R^{16})R^{17}$, $C(=NN(C(=O)OR^{14})R^{16})R^{17}$, $C(=NN(C(=O)NR^{16}R^{17})R^{16})R^{17}$, $C(=NOR^{16})NR^{16}R^{17}$, $ON=CR^{16}R^{17}$, $ONR^{16}R^{17}$, $S(=O)(=NR^{16})R^{17}$, $SO_2NR^{16}C(=O)NR^{17}R^{18}$, $P(=X^2)R^{13}R^{14}$, $OP(=X^2)R^{13}R^{14}$, $OP(=X^2)(OR^{13})R^{14}$, $OP(=X^2)(OR^{13})OR^{14}$, $N=CR^{16}R^{17}$, $NR^{16}N=CR^{17}R^{18}$, $NR^{16}NR^{17}R^{18}$, $NR^{16}C(=X^2)NR^{17}R^{18}$, $NR^{16}C(=NR^{16})NR^{17}R^{18}$, $NR^{16}NR^{16}C(=X^2)NR^{17}R^{18}$ or $NR^{16}NR^{16}SO_2NR^{17}R^{18}$; or each $R^4$ is independently $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cyclolkylalkylalkoxy, $C_3$-$C_{10}$ cycloalkoxyalkyl, $C_3$-$C_{10}$ cycloalkoxyalkoxy, $C_2$-$C_8$ alkenyloxy, $C_3$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkysulfonyl, $C_4$-$C_0$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{12}$; or each $R^4$ is independently $Z^1Q^1$; or two $R^4$ substituents are taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring optionally substituted with up to 3 substituents independently selected from the group consisting of halogen, cyano, hydroxy, amino, nitro, C(=O)OH, C(=O)NH$_2$, SO$_2$NH$_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl, $C_2$-$C_6$ haloalkylcarbonyl, $C_1$-$C_4$ alkylthio, $C_1$-$C_4$ alkylsulfinyl and $C_1$-$C_4$ alkylsulfonyl;

each $R^5$ is independently halogen, cyano, nitro, $C_1$-$C_3$ alkyl, $C_1$-$C_3$ haloalkyl, $C_2$-$C_3$ alkenyl, $C_1$-$C_3$ haloalkenyl, $C_2$-$C_3$ alkynyl, C(=O)OR$^8$, C(=O)NR$^9$R$^{10}$ or $Z^1Q^2$;

each $R^6$ is independently halogen, cyano, nitro, CHO, C(=O)OH, C(=O)NH$_2$, C(=O)R$^7$, C(=O)OR$^8$, C(=O)NR$^9$R$^{10}$, OR$^8$, S(O)$_n$R$^7$, SO$_2$NR$^9$R$^{10}$ or Si(R$^7$)$_3$; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, $C_2$-$C_6$ alkylcarbonyl or $C_2$-$C_6$ alkoxycarbonyl, each unsubstituted or substituted with at least one substituent independently selected from the group consisting of halogen, cyano, nitro, CHO, C(=O)OH, C(=O)NH$_2$, C(=O)R$^7$, C(=O)OR$^8$, C(=O)NR$^9$R$^{10}$, OR$^8$, S(O)$_n$R$^7$, SO$_2$NR$^9$R$^{10}$ and Si(R$^7$)$_3$;

each $R^7$, $R^8$, $R^9$ and $R^{10}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, C(=O)OH, C(=O)NH$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_1$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, C(=O)OH, C(=O)NH$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $Z^1$ is independently a direct bond; or a 1- to 4-atom chain containing chain members selected from carbon atoms and up to 2 heteroatoms independently selected from up to 2 O, up to 2 S, and up to 2 N, wherein up to 2 carbon atom chain members are independently selected from C(=O) and C(=S) and the sulfur atom chain members are independently selected from S(=O)$_n$, each 1- to 4-atom chain being unsubstituted or substituted with up to 4 substituents independently selected from $R^5$, or substituted with up to 9 halogen when $R^5$ is halogen;

each $X^2$ is independently O or S;

each $Q^1$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=NR$^{19}$)$_z$, each ring or ring system optionally substituted with up to 4 substituents independently selected from the group consisting of halogen, cyano, nitro, CHO, C(=O)OH, C(=O)NH$_2$, C(=O)R$^7$, C(=O)OR$^8$, C(=O)NR$^9$R$^{10}$, OR$^8$, S(O)$_n$R$^7$, SO$_2$NR$^9$R$^{10}$, Si(R$^7$)$_3$ and $R^{11}$;

each $Q^2$ is independently phenyl or a 5- or 6-membered heteroaromatic ring, each unsubstituted or substituted with up to 3 substituents independently selected from the group consisting of halogen, cyano, nitro, CHO, C(=O)OH, C(=O)NH$_2$, C(=O)R$^7$, C(=O)OR$^8$, C(=O)NR$^9$R$^{10}$, OR$^8$, S(O)$_n$R$^7$, SO$_2$NR$^9$R$^{10}$, Si(R$^7$)$_3$ and $R^{11}$;

each $R^{11}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, C(=O)OH, C(=O)NH, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, C(=O)OH, C(=O)NH$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $R^{12}$ is independently halogen, cyano, nitro, CHO, C(=O)OH, C(=O)$NH_2$, C(=O)$R^7$, C(=O)$OR^8$, C(=O)$NR^9R^{10}$, $OR^8$, S(O)$_n$$R^7$, $SO_2NR^9R^{10}$, Si($R^7$)$_3$ or $Z^1Q^2$;

each $R^{13}$, $R^{14}$ and $R^{15}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{12}$; or $Q^2$;

each $R^{16}$, $R^{17}$ and $R^{18}$ is independently H, $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{12}$; or $Q^2$;

each $R^{19}$ is independently H, cyano, OCN. SCN, CHO, C(=O)OH, C(=O)$NH_2$, C(=S)$NH_2$, $SO_2NH_2$, C(=O)$R^{13}$, C(=O)$OR^{13}$, $NHR^{13}$, $NR^{13}R^{14}$, C(=O)$NR^{16}R^{14}$, C(=S)$NR^{16}R^{14}$, $SO_2NR^{16}R^{14}$, OC(=O)$R^{16}$, OC(=O)$OR^{13}$, OC(=O)$NR^{16}R^{14}$, N($R^{16}$)C(=O)$R^{16}$, N($R^{16}$)C(=O)$OR^{14}$, N($R^{16}$)C(=O)$NR^{16}R^{17}$, $OSO_2R^{13}$, $OSO_2NR^{16}R^{17}$, $NR^{16}SO_2R^{13}$, $NR^{16}SO_2NR^{16}R^{17}$, Si($R^{13}R^{14}R^{15}$) or $Z^1Q^2$; or $C_{1-8}$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cyclooakylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkysulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_1$-$C_8$ alkynylthio, $C_2$-$C_8$ alkynylsulfinyl or $C_2$-$C_8$ alkynylsulfonyl, each unsubstituted or substituted with at least one substituent independently selected from $R^{12}$;

each n is independently 0, 1 or 2; and u and z in each instance of S(=O)$_u$(=$NR^{19}$)$_z$ are independently 0, 1 or 2, provided that the sum of u and z in each instance of S(=O)(=$NR^{19}$)$_z$ is 0, 1 or 2.

This invention also provides a composition comprising a compound of Formula 1, an N-oxide or a salt thereof, and at least one additional component selected from the group consisting of surfactants, solid diluents and liquid diluents. In one embodiment, this invention also provides a composition for controlling an invertebrate pest comprising a compound of Formula 1, an N-oxide or a salt thereof, and at least one additional component selected from the group consisting of surfactants, solid diluents and liquid diluents, said composition optionally further comprising at least one additional biologically active compound or agent.

This invention provides a method for controlling an invertebrate pest comprising contacting the invertebrate pest or its environment with a biologically effective amount of a compound of Formula 1, an N-oxide or a salt thereof, (e.g., as a composition described herein). This invention also relates to such method wherein the invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent.

This invention also provides a method for protecting a seed from an invertebrate pest comprising contacting the seed with a biologically effective amount of a compound of Formula 1, an N-oxide or a salt thereof, (e.g., as a composition described herein). This invention also relates to the treated seed. This invention further provides a method for protecting an animal from an invertebrate parasitic pest comprising administering to the animal a parasiticidally effective amount of a compound of Formula 1, an N-oxide or a salt thereof, (e.g., as a composition described herein). This invention also provides for the use of a compound of Formula 1, an N-oxide or a salt thereof, (e.g., as a composition described herein) in protecting an animal from an invertebrate pest.

This invention also provides a method for increasing vigor of a crop plant comprising contacting the crop plant, the seed from which the crop plant is grown or the locus (e.g., growth medium) of the crop plant with a biologically effective amount of a compound of Formula 1 (e.g., as a composition described herein).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods, nematodes and helminths of economic importance as pests. The term "arthropod" includes insects, mites, spiders, scorpions, centipedes, millipedes, pill bugs and symphylans.

The term "gastropod" includes snails, slugs and other Stylommatophora. The term "nematode" includes members of the phylum Nematoda, such as phytophagous nematodes and helminth nematodes parasitizing animals. The term "helminth" includes all of the parasitic worms, such as roundworms (phylum Nematoda), heartworms (phylum Nematoda, class Secernentea), flukes (phylum Platyhelminthes, class Tematoda), acanthocephalans (phylum Acanthocephala), and tapeworms (phylum Platyhelminthes, class Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of maize or corn, soybeans and other legumes, rice, cereal (e.g., wheat, oats, barley, rye and rice), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (e.g., berries and cherries) and other specialty crops (e.g., canola, sunflower and olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

The term "crop vigor" refers to rate of growth or biomass accumulation of a crop plant. An "increase in vigor" refers to an increase in growth or biomass accumulation in a crop plant relative to an untreated control crop plant. The term "crop yield" refers to the return on crop material, in terms of both quantity and quality, obtained after harvesting a crop plant. An "increase in crop yield" refers to an increase in crop yield relative to an untreated control crop plant.

The term "biologically effective amount" refers to the amount of a biologically active compound (e.g., a compound of Formula 1) sufficient to produce the desired biological effect when applied to (i.e. contacted with) an invertebrate pest to be controlled or its environment, or to a plant, the seed from which the plant is grown, or the locus of the plant (e.g., growth medium) to protect the plant from injury by the invertebrate pest or for other desired effect (e.g., increasing plant vigor).

In the structure of Formula 1, the variable A is defined as a 5-, 6- or 7-membered ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and the sulfur atom ring members are independently selected from $S(=O)_n$, each ring unsubstituted or substituted with up to 3 substituents independently selected from $R^3$. These 5-, 6- and 7-membered rings include the imidazolium nitrogen and carbon atoms to which the A ring members are attached to form said rings, as depicted in the structures below, wherein R represents a ring member selected as defined above, and a is 0, 1, 2 or 3.

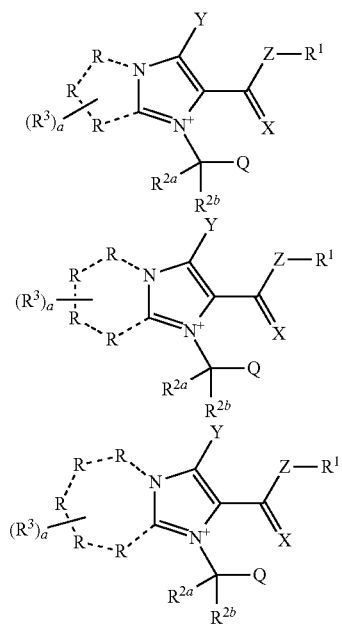

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Cycloalkyl" includes, for example, cyclopropyl, cyclobutyl, cyclopentyl and cyclohexyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C-$, $ClCH_2-$, $CF_3CH_2-$ and $CF_3CCl_2-$. The terms "halocycloalkyl", "haloalkoxy", "haloalkylthio", "haloalkenyl" and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$.

The chemical abbreviations $S(O)$ and $S(=O)$ as used herein represent a sulfinyl moiety. The chemical abbreviations $SO_2$, $S(O)_2$ and $S(=O)_2$ as used herein represent a sulfonyl moiety. The chemical abbreviations $C(O)$ and $C(=O)$ as used herein represent a carbonyl moiety. The chemical abbreviations $CO_2$, $C(O)O$ and $C(=O)O$ as used herein represent an oxycarbonyl moiety. "CHO" means formyl.

The total number of carbon atoms in a substituent group is indicated by the "$C_i$-$C_j$" prefix. For example, $C_1$-$C_6$ alkyl designates methyl, ethyl, and the various propyl, butyl, pentyl and hexyl isomers.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive. When a group contains a substituent which can be hydrogen, then when this substituent is taken as hydrogen, it is recognized that this is equivalent to said group being unsubstituted. When one or more positions on a group are said to be "not substituted" or "unsubstituted", then hydrogen atoms are attached to take up any free valency.

Unless otherwise indicated, a "ring" or "ring system" as a component of Formula 1 (e.g., substituent $R^1$) is carbocyclic or heterocyclic. The term "ring system" denotes two or more fused rings. The terms "bicyclic ring system" and "fused bicyclic ring system" denote a ring system consisting of two fused rings, which can be "ortho-fused", "bridged bicyclic" or "spirobicyclic". An "ortho-fused bicyclic ring system" denotes a ring system wherein the two constituent rings have two adjacent atoms in common. A "bridged bicyclic ring system" is formed by bonding a segment of one or more atoms to nonadjacent ring members of a ring. A "spirobicyclic ring system" is formed by bonding a segment of two or more atoms to the same ring member of a ring. The term "fused heterobicyclic ring system" denotes a fused bicyclic ring system in which at least one ring atom is not carbon. The term "ring member" refers to an atom or other moiety (e.g., $C(=O)$, $C(=S)$, $S(O)$ or $S(O)_2$) forming the backbone of a ring or ring system.

The terms "carbocyclic ring", "carbocycle" or "carbocyclic ring system" denote a ring or ring system wherein the atoms forming the ring backbone are selected only from carbon. The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a carbocyclic ring or heterocyclic ring can be a saturated or unsaturated ring. "Saturated" refers to a ring having a backbone consisting of atoms linked to one another by single bonds; unless otherwise specified, the remaining atom valences are occupied by hydrogen atoms. Unless otherwise stated, an "unsaturated ring" may be partially unsaturated or fully unsaturated. The expression "fully unsaturated ring" means a ring of atoms in which the bonds between atoms in the ring are single or double bonds according to valence bond theory and furthermore the bonds between atoms in the ring include as many double bonds as possible without double bonds being cumulative (i.e. no $C=C=C$ or $C=C=N$). The term "partially unsaturated ring" denotes a ring comprising at least one ring member bonded to an adjacent ring member through a double bond and which conceptually potentially accommodates a number of non-cumulated double bonds between adjacent ring members (i.e. in its fully unsaturated counterpart form) greater than the number of double bonds present (i.e. in its partially unsaturated form).

Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and in which (4n+2) π electrons, where n is a positive integer, are associated with the ring to comply with Hückel's rule. The term "aromatic ring system" denotes a carbocyclic or heterocyclic ring system in which at least one ring of the ring system is aromatic. When a fully unsaturated carbocyclic ring satisfies Hückel's rule, then said ring is also called an "aromatic ring" or "aromatic carbocyclic ring".

The term "aromatic carbocyclic ring system" denotes a carbocyclic ring system in which at least one ring of the ring system is aromatic. When a fully unsaturated heterocyclic ring satisfies Hückel's rule, then said ring is also called a "heteroaromatic ring", "aromatic heterocyclic ring" or "heterocyclic aromatic ring". The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" denotes a carbocyclic ring in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted" Unless otherwise indicated, an optionally substituted group may have a substituent at each substitutable position of the group, and each substitution is independent of the other.

When a substituent is a 5- or 6-membered nitrogen-containing heterocyclic ring, it may be attached to the remainder of Formula 1 though any available carbon or nitrogen ring atom, unless otherwise described. As noted above, $R^1$ can be (among others) phenyl optionally substituted with one or more substituents selected from a group of substituents as defined in the Summary of Invention. An example of phenyl optionally substituted with one to five substituents is the ring illustrated as U-1 in Exhibit 1, wherein $R^v$ is $R^x$ as defined in the Summary of the Invention for $R^1$ and r is an integer from 0 to 5.

As noted above, $R^1$ can be (among others) a 5- or 6-membered heterocyclic aromatic ring, optionally substituted with one or more substituents selected from a group of substituents as defined in the Summary of Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for $R^1$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

U-1
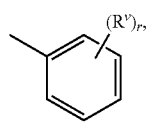

U-2
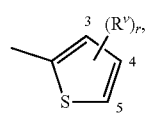

U-3
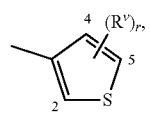

U-4
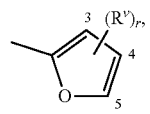

U-5
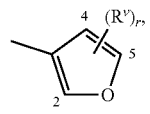

U-6
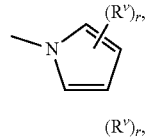

U-7
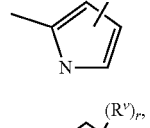

U-8
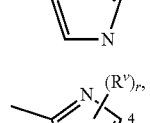

U-9
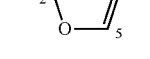

-continued

U-10
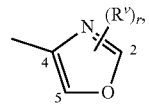

U-11
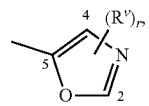

U-12
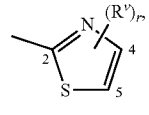

U-13
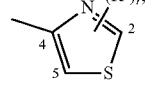

U-14
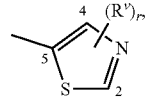

U-15
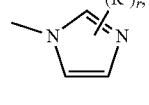

U-16
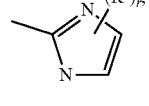

U-17
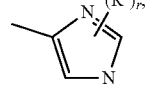

U-18
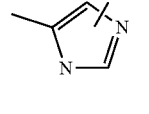

U-19
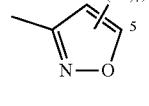

U-20
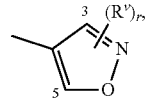

U-21
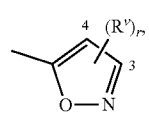

U-22

| | |
|---|---|
| 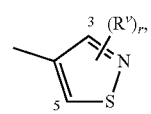 | U-23 |
| 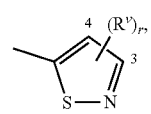 | U-24 |
| 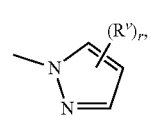 | U-25 |
| 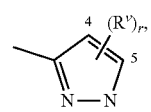 | U-26 |
| 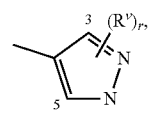 | U-27 |
| 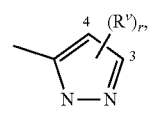 | U-28 |
| 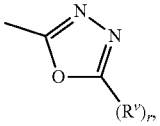 | U-29 |
| 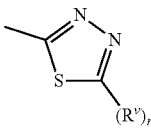 | U-30 |
| 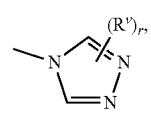 | U-31 |
| 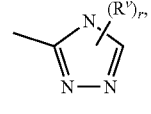 | U-32 |
| 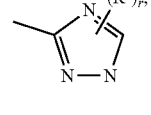 | U-33 |
| 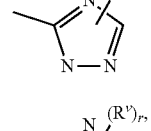 | U-34 |
| 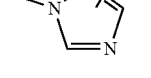 | U-35 |
| 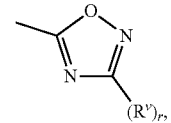 | U-36 |
| 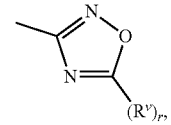 | U-37 |
| 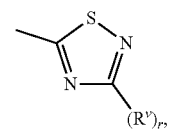 | U-38 |
| 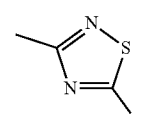 | U-39 |
| 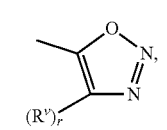 | U-40 |
| 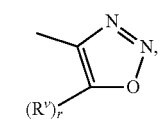 | U-41 |
| 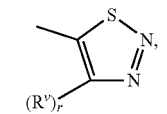 | U-42 |
| 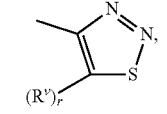 | U-43 |
| 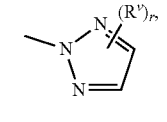 | U-44 |
| 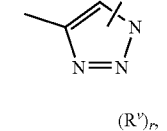 | U-45 |
| 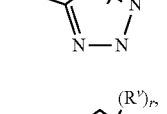 | U-46 |
| | U-47 |

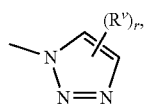
U-48

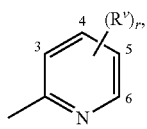
U-49

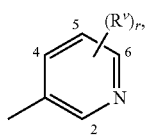
U-50

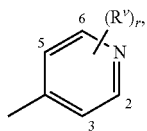
U-51

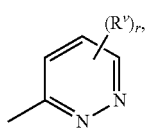
U-52

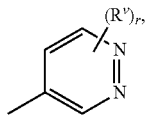
U-53

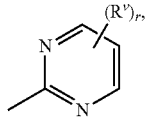
U-54

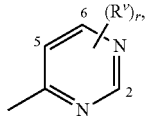
U-55

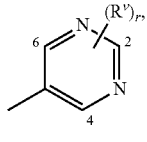
U-56

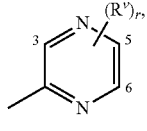
U-57

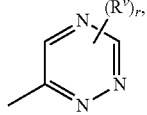
U-58

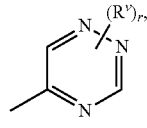
U-59

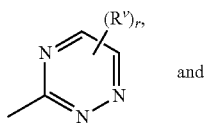 and
U-60

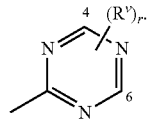
U-61

Although $R^v$ groups are shown in the structures U-1 through U-61, it is noted that they do not need to be present since they are optional substituents. Note that when $R_v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. For a comprehensive discussion of all aspects of stereoisomerism, see Ernest L. Eliel and Samuel H. Wilen, *Stereochemistry of Organic Compounds*, John Wiley & Sons, 1994.

This invention comprises all stereoisomers, conformational isomers and mixtures thereof in all proportions as well as isotopic forms such as deuterated compounds.

One skilled in the art will appreciate that not all nitrogen-containing heterocycles can form N-oxides since the nitrogen requires an available lone pair for oxidation to the oxide;

one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grinmmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of invertebrate pests. The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures. Compounds of this invention may exist as one or more crystalline polymorphs. This invention comprises both individual polymorphs and mixtures of polymorphs, including mixtures enriched in one polymorph relative to others. For a comprehensive discussion of polymorphism see R. Hilfiker, Ed., *Polymorphism in the Pharmaceutical Industry*, Wiley-VCH, Weinheim, 2006.

Embodiments of the present invention as described in the Summary of the Invention include those described below. In the following Embodiments, reference to "a compound of Formula 1" includes the definitions of substituents specified in the Summary of the Invention unless further defined in the Embodiments.

EMBODIMENT 1

A compound of Formula 1 wherein A is a 5- or 6-membered ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring unsubstituted or substituted with up to 3 substituents independently selected from R$^3$.

EMBODIMENT 2

A compound of Formula 1 wherein A is a 5-membered ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring unsubstituted or substituted with up to 3 substituents independently selected from R$^3$.

EMBODIMENT 3

A compound of Formula 1 wherein A is a 6-membered ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring unsubstituted or substituted with up to 3 substituents independently selected from R$^3$.

EMBODIMENT 4

A compound of Formula 1 wherein A is a 5-membered ring containing ring members selected from carbon atoms and up to 3 heteroatoms independently selected from up to 1 O, up to 1 S, and up to 2 N, wherein up to 1 carbon atom ring members are independently selected from C(=O) and C(=S) and the sulfur atom ring members are independently selected from S(=O)$_n$, each ring unsubstituted or substituted with up to 3 substituents independently selected from R$^3$.

EMBODIMENT 5

A compound of Formula 1 wherein A is a 6-membered ring containing ring members selected from carbon atoms and up to 3 heteroatoms independently selected from up to 1 O, up to 1 S, and up to 2 N, wherein up to 1 carbon atom ring members are independently selected from C(=O) and C(=S) and the sulfur atom ring members are independently selected from S(=O)$_n$, each ring unsubstituted or substituted with up to 3 substituents independently selected from R$^3$.

EMBODIMENT 6

A compound of Formula 1 wherein A is a 5-membered ring containing ring members selected from carbon atoms and up to 2 heteroatoms independently selected from up to 1 O, up to 1 S, and up to 2 N, each ring unsubstituted or substituted with up to 3 substituents independently selected from R$^3$.

EMBODIMENT 7

A compound of Formula 1 wherein A is a 6-membered ring containing ring members selected from carbon atoms and up to 2 heteroatoms independently selected from up to 1 O, up to 1 S, and up to 2 N, each ring unsubstituted or substituted with up to 3 substituents independently selected from R$^3$.

EMBODIMENT 8

A compound of Formula 1 having the structure of Formula 1-1

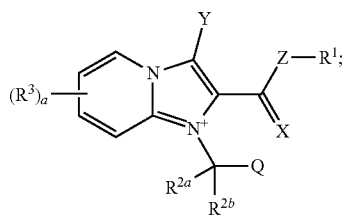

1-1 wherein a is 0, 1, 2 or 3.

EMBODIMENT 8a

A compound of Formula 1 having the structure of Formula 1-2

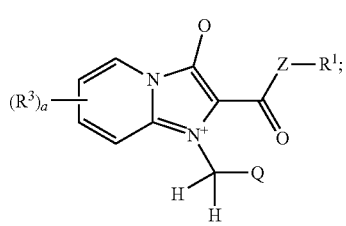

1-2 wherein R$^3$ is F, Cl or CH$_3$, and a is 0 or 1.

EMBODIMENT 8b

A compound of Formula 1 having the structure of Formula 1-3 (Formula 1-2 wherein Z is a direct bond)

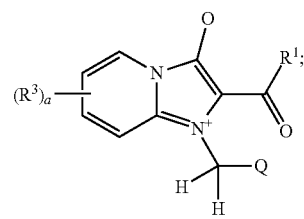

1-3 wherein R$^3$ is F, Cl or CH$_3$, and a is 0 or 1.

EMBODIMENT 8c

A compound of Formula 1 having the structure of Formula 1-4

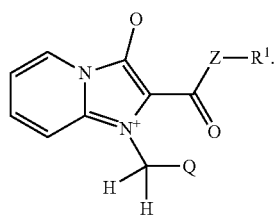

1-4

EMBODIMENT 8d

A compound of Formula 1 having the structure of Formula 1-5 (Formula 1-4 wherein Z is a direct bond)

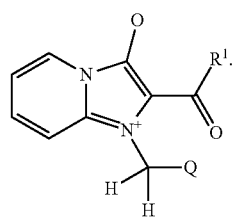

1-5

EMBODIMENT 9

A compound of Formula 1 wherein one of X and Y is oxygen and one is sulfur.

EMBODIMENT 9a

A compound of Formula 1 wherein X and Y are oxygen.

EMBODIMENT 10

A compound of Formula 1 wherein Z is a direct bond.

EMBODIMENT 11

A compound of Formula 1 wherein Z is a 1- to 4-atom chain containing chain members selected from carbon atoms and up to 2 heteroatoms independently selected from up to 2 O, up to 2 S, and up to 2 N, wherein up to 2 carbon atom chain members are independently selected from C(=O) and C(=S) and the sulfur atom chain members are independently selected from S(=O)$_n$, each 1- to 4-atom chain being unsubstituted or substituted with up to 4 substituents independently selected from $R^5$, or substituted with up to 9 halogen when $R^5$ is halogen.

EMBODIMENT 12

A compound of Formula 1 wherein Z is a 1- to 4-atom chain containing chain members selected from carbon atoms and up to 1 heteroatom independently selected from O, S, and N, wherein up to 1 carbon atom chain member is independently selected from C(=O) and C(=S) and the sulfur atom chain members are independently selected from S(=O)$_n$, each 1- to 4-atom chain being unsubstituted or substituted with up to 4 substituents independently selected from $R^5$, or substituted with up to 9 halogen when $R^5$ is halogen.

EMBODIMENT 13

A compound of Formula 1 wherein Z is a 1- to 4-atom chain containing carbon atoms wherein up to 1 carbon atom chain member is independently selected from C(=O) and C(=S), each 1- to 4-atom chain being unsubstituted or substituted with up to 4 substituents independently selected from $R^5$, or substituted with up to 9 halogen when $R^5$ is halogen.

EMBODIMENT 13a

A compound of Formula 1 wherein Z is $CH_2$.

EMBODIMENT 13b

A compound of Formula 1 wherein Z is O.

EMBODIMENT 14

A compound of Formula 1 wherein $R^1$ is H or halogen.

EMBODIMENT 14a

A compound of Formula 1 wherein Z is 1- to 4-carbon atom chain substituted with up to 8 halogen, and $R^1$ is H or halogen.

EMBODIMENT 14b

A compound of Formula 1 wherein Z is 1- to 4-carbon atom chain substituted with up to 8 F, and $R^1$ is H or F.

EMBODIMENT 14c

A compound of Formula 1 wherein Z is $CH_2$ and $R^1$ is halogen.

EMBODIMENT 14d

A compound of Formula 1 wherein Z is $CH_2$ and $R^1$ is Cl.

EMBODIMENT 15

A compound of Formula 1 wherein $R^1$ is a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=NR$^{19}$)$_z$, each ring or ring system unsubstituted or substituted with up to 8 substituents independently selected from $R^4$.

EMBODIMENT 15a

A compound of Formula 1 wherein $R^1$ is $C_3$-$C_7$ cycloalkyl, unsubstituted or substituted with up to 4 substituents independently selected from $R^4$.

EMBODIMENT 15b

A compound of Formula 1 wherein Z is a direct bond, and $R^1$ is $C_3$-$C_7$ cycloalkyl, unsubstituted or substituted with up to 4 substituents independently selected from $R^4$.

EMBODIMENT 16

A compound of Formula 1 wherein $R^1$ is a 5- to 7-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=NR$^{19}$)$_z$, each ring or ring system unsubstituted or substituted with up to 8 substituents independently selected from $R^4$.

EMBODIMENT 17

A compound of Formula 1 wherein $R^1$ is a 5- to 7-membered ring, each ring containing ring members selected from carbon atoms and up to 3 heteroatoms independently selected from up to 1 O, up to 1 S, and up to 3 N, wherein up to 1 carbon atom ring members are independently selected from C(=O) and C(=S) and the sulfur atom ring member is independently selected from S(=O)$_u$(=NR$^{19}$)$_z$, each ring unsubstituted or substituted with up to 4 substituents independently selected from $R^4$.

EMBODIMENT 18

A compound of Formula 1 wherein $R^1$ is a 7- to 11-membered ring system, each ring system containing ring members selected from carbon atoms and up to 4 heteroatoms independently selected from up to 1 O, up to 1 S, and up to 4 N, wherein up to 1 carbon atom ring members are independently selected from C(=O) and C(=S) and the sulfur atom ring member is independently selected from S(=O)$_u$(=NR$^{19}$)$_z$, each ring system unsubstituted or substituted with up to 4 substituents independently selected from $R^4$.

EMBODIMENT 19

A compound of Formula 1 wherein $R^1$ is a 5- or 6-membered heteroaromatic ring, each ring containing ring members selected from carbon atoms and up to 3 heteroatoms independently selected from up to 1 O, up to 1 S, and up to 3 N, wherein up to 1 carbon atom ring members are independently selected from C(=O) and C(=S) and the sulfur atom ring member is independently selected from S(=O)$_u$(=NR$^{19}$)$_z$, each ring is unsubstituted or substituted with up to 4 substituents independently selected from R$^4$.

EMBODIMENT 19a

A compound of Formula 1 wherein R$^1$ is phenyl; or R$^1$ is a 5- or 6-membered heteroaromatic ring, each ring containing ring members selected from carbon atoms and up to 3 heteroatoms independently selected from up to 1 O, up to 1 S, and up to 3 N, wherein up to 1 carbon atom ring members are independently selected from C(=O) and C(=S) and the sulfur atom ring member is independently selected from S(=O)$_u$(=NR$^{19}$)$_z$, each ring is unsubstituted or substituted with up to 4 substituents independently selected from R$^4$.

EMBODIMENT 19b

A compound of Formula 1 wherein R$^1$ is phenyl; or R$^1$ is a 6-membered heteroaromatic ring containing ring members selected from carbon atoms and up to 3 N, each phenyl or 6-membered heteroaromatic ring being unsubstituted or substituted with up to 4 substituents independently selected from R$^4$.

EMBODIMENT 19c

A compound of Formula 1 wherein R$^1$ is phenyl or pyridinyl, each unsubstituted or substituted with up to 4 substituents independently selected from R$^4$.

EMBODIMENT 19d

A compound of Formula 1 wherein R$^1$ is phenyl, unsubstituted or substituted with up to 4 substituents independently selected from R$^4$.

EMBODIMENT 19e

A compound of Formula 1 wherein R$^1$ is pyridinyl, each unsubstituted or substituted with up to 4 substituents independently selected from R$^4$.

EMBODIMENT 19a1

A compound of Formula 1 wherein Z is a direct bond, and R$^1$ is phenyl; or R$^1$ is a 5- or 6-membered heteroaromatic ring, each ring containing ring members selected from carbon atoms and up to 3 heteroatoms independently selected from up to 1 O, up to 1 S, and up to 3 N, wherein up to 1 carbon atom ring members are independently selected from C(=O) and C(=S) and the sulfur atom ring member is independently selected from S(=O)$_u$(=NR$^{19}$)$_z$, each ring is unsubstituted or substituted with up to 4 substituents independently selected from R$^4$.

EMBODIMENT 19b1

A compound of Formula 1 wherein Z is a direct bond, and R$^1$ is phenyl; or R$^1$ is a 6-membered heteroaromatic ring containing ring members selected from carbon atoms and up to 3 N, each phenyl or 6-membered heteroaromatic ring being unsubstituted or substituted with up to 4 substituents independently selected from R$^4$.

EMBODIMENT 9c1

A compound of Formula 1 wherein Z is a direct bond, and R$^1$ is phenyl or pyridinyl, each unsubstituted or substituted with up to 4 substituents independently selected from R$^4$.

EMBODIMENT 19d1

A compound of Formula 1 wherein Z is a direct bond, and R$^1$ is phenyl, unsubstituted or substituted with up to 4 substituents independently selected from R$^4$.

EMBODIMENT 19e1

A compound of Formula 1 wherein Z is a direct bond, and R$^1$ is pyridinyl, each unsubstituted or substituted with up to 4 substituents independently selected from R$^4$.

EMBODIMENT 20

A compound of Formula 1 or any one of Embodiments 19-19e1 wherein each R$^4$ is independently C$_1$-C$_4$ alkyl, C$_1$-C$_4$ alkoxy or C$_1$-C$_4$ alkylthio, each unsubstituted or substituted with halogen.

EMBODIMENT 21

A compound of Formula 1 wherein R$^{2a}$ and R$^{2b}$ are each independently H, halogen or C$_1$-C$_2$ alkyl; or R$^{2a}$ and R$^{2b}$ are taken together to form a 3- to 4-membered ring containing carbon atoms and up to one heteroatom selected from O, N and S(O)$_n$.

EMBODIMENT 21a

A compound of Formula 1 wherein R$^{2a}$ and R$^{2b}$ are each independently H or methyl.

EMBODIMENT 22

A compound of Formula 1 wherein R$^{2a}$ and R$^{2b}$ are H.

EMBODIMENT 23

A compound of Formula 1 wherein Q is a 5-membered heteroaromatic ring, unsubstituted or substituted with up to 3 substituents independently selected from R$^6$.

EMBODIMENT 24

A compound of Formula 1 wherein Q is a 6-membered heteroaromatic ring, unsubstituted or substituted with up to 3 substituents independently selected from R$^6$.

EMBODIMENT 25

A compound of Formula 1 wherein Q is 2-chloro-5-thiazolyl, 2-bromo-5-thiazolyl, 2-fluoro-5-thiazolyl, 2-methyl-5-thiazolyl, 2-(difluoromethyl)-5-thiazolyl, 2-(trifluoromethyl)-5-thiazolyl or 5-thiazolyl.

EMBODIMENT 26

A compound of Formula 1 wherein Q is 2-chloro-5-pyridinyl, 2-fluoro-5-pyridinyl, 2-bromo-5-pyridinyl, 2-methyl-5-pyridinyl, 2-(difluoromethyl)-5-pyridinyl, 2-(trifluoromethyl)-5-pyridinyl or 3-pyridinyl.

EMBODIMENT 27

A compound of Formula 1 wherein Q is 5-pyrimidinyl, 2-chloro-5-pyrimidinyl, 2-fluoro-5-pyrimidinyl, 2-bromo-5-pyrimidinyl, 2-methyl-5-pyrimidinyl, 2-(difluoromethyl)-5-pyrimidinyl or 2-(trifluoromethyl)-5-pyrimidinyl.

EMBODIMENT 28

A compound of Formula 1 wherein Q is

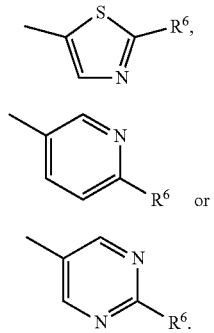

EMBODIMENT 28a

A compound of Embodiment 28 wherein $R^6$ is 1H, halogen, $C_1$-$C_4$ alkyl or $C_1$-$C_4$ haloalkyl.

EMBODIMENT 28b

A compound of Embodiment 28 wherein $R^6$ is H, F, Cl, Br, $CH_3$, $CHF_2$ or $CF_3$.

EMBODIMENT 29

A compound of Formula 1 wherein Q is

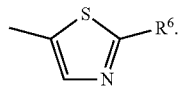

EMBODIMENT 29a

A compound of Embodiment 29 wherein $R^6$ is H, halogen, $C_1$-$C_4$ alkyl or $C_1$-$C_4$ haloalkyl.

EMBODIMENT 29b

A compound of Embodiment 29 wherein $R^6$ is H, F, Cl, Br, $CH_3$, $CHF_2$ or $CF_3$.

EMBODIMENT 29c

A compound of Formula 1 wherein Q is 2-chloro-5-thiazolyl.

Embodiments of this invention, including Embodiments 1-29c above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-29c above as well as any other embodiments described herein, and any combination thereof, pertain to the compositions and methods of the present invention.

Combinations of Embodiments 1-29c are illustrated by:

EMBODIMENT A

A compound of Formula 1 having the structure of Formula 1-1

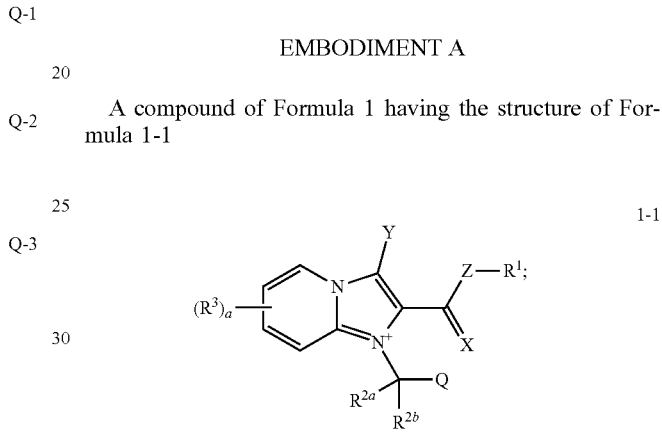

wherein a is 0, 1, 2 or 3;
$R^{2a}$ and $R^{2b}$ are H; and
Q is

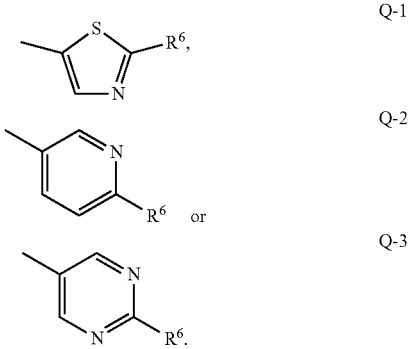

EMBODIMENT A 1

The compound of Embodiment A wherein
$R^6$ is H, halogen, $C_1$-$C_4$ alkyl or $C_1$-$C_4$ haloalkyl.

EMBODIMENT A2

The compound of Embodiment A1 wherein
$R^6$ is H, F, Cl, Br, $CH_3$, $CHF_2$ or $CF_3$.

EMBODIMENT B

A compound of Formula 1 having the structure of Formula 1-3

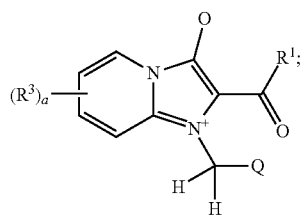

1-3 wherein R³ is F, Cl or CH₃, and a is 0 or 1; and
R¹ is phenyl or pyridinyl, each unsubstituted or substituted with up to 4 substituents independently selected from R⁴.

EMBODIMENT B1

The compound of Embodiment B wherein R¹ is phenyl, unsubstituted or substituted with up to 4 substituents independently selected from R⁴.

EMBODIMENT B2

The compound of Embodiment B or B1, wherein Q is

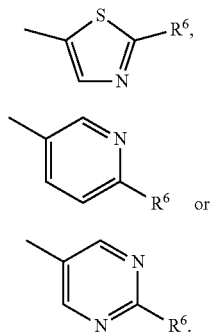

Q-1

Q-2

Q-3

EMBODIMENT B3

The compound of Embodiment B2 wherein R⁶ is H, halogen, C₁-C₄ alkyl or C₁-C₄ haloalkyl.

EMBODIMENT B4

The compound of Embodiment B3 wherein Q is

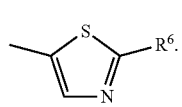

Q-1

EMBODIMENT B5

The compound of Embodiment B4 wherein R⁶ is H, F, Cl, Br, CH₃, CHF₂ or CF₃.

EMBODIMENT B6

The compound of Embodiment B5 wherein R⁶ is Cl.

EMBODIMENT C

A compound of Formula 1 having the structure of Formula 1-5

1-5

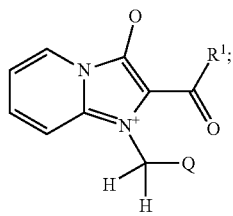

wherein Q is

Q-1

Q-2

Q-3

EMBODIMENT C1

The compound of Embodiment C wherein R⁶ is H, halogen, C₁-C₄ alkyl or C₁-C₄ haloalkyl.

EMBODIMENT C2

The compound of Embodiment C1 wherein R⁶ is H, F, Cl, Br, CH₃, CHF₂ or CF₃.

EMBODIMENT C3

The compound of Embodiment C2 wherein Q is Q-1; and
R⁶ is Cl.

EMBODIMENT D

A compound of Formula 1 having the structure of Formula 1-5

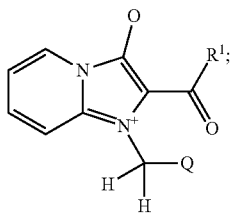

1-5 wherein $R^1$ is phenyl or pyridinyl, each unsubstituted or substituted with up to 4 substituents independently selected from $R^4$.

EMBODIMENT D1

The compound of Embodiment D wherein $R^1$ is phenyl, unsubstituted or substituted with up to 4 substituents independently selected from $R^4$.

EMBODIMENT D2

The compound of Embodiment D or D1, wherein Q is

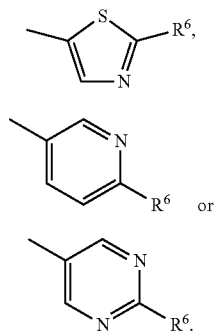

Q-1

Q-2

Q-3

EMBODIMENT D3

The compound of Embodiment D2 wherein $R^6$ is H, halogen, $C_1$-$C_4$ alkyl or $C_1$-$C_4$ haloalkyl.

EMBODIMENT D4

The compound of Embodiment D3 wherein Q is

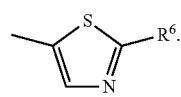

Q-1

EMBODIMENT D5

The compound of Embodiment D4 wherein $R^6$ is H, F, Cl, Br, $CH_3$, $CHF_2$ or $CF_3$.

EMBODIMENT D6

The compound of Embodiment D5 wherein $R^6$ is Cl.

EMBODIMENT D7

The compound of Embodiment D or D1, wherein each $R^4$ is independently $C_1$-$C_4$ alkyl, $C_1$-$C_4$ alkoxy or $C_1$-$C_4$ alkylthio, each unsubstituted or substituted with halogen.

EMBODIMENT E

A compound of Formula 1 having the structure of Formula 1-3

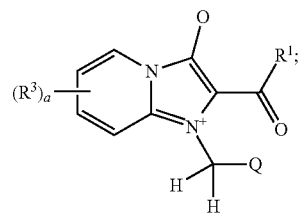

1-3 wherein $R^3$ is F, Cl or $CH_3$, and a is 0 or 1;
$R^1$ is phenyl or pyridinyl, each unsubstituted or substituted with up to 4 substituents independently selected from $R^4$;
Q is

Q-1

Q-2

Q-3 and
$R^6$ is H, halogen, $C_1$-$C_4$ alkyl or $C_1$-$C_4$ haloalkyl.

EMBODIMENT E1

A compound of Embodiment E wherein $R^1$ is phenyl, unsubstituted or substituted with up to 4 substituents independently selected from $R^4$.

EMBODIMENT F

A compound of Formula 1 having the structure of Formula 1-3

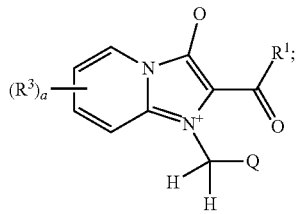

1-3 wherein $R^3$ is F, Cl or $CH_3$, and a is 0 or 1;
$R^1$ is phenyl or pyridinyl, each unsubstituted or substituted with up to 4 substituents independently selected from $R^4$;
Q is

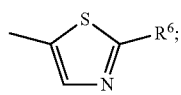

Q-1 and
$R^6$ is H, halogen, $C_1$-$C_4$ alkyl or $C_1$-$C_4$ haloalkyl.

EMBODIMENT F1

A compound of Embodiment F wherein $R^1$ is phenyl, unsubstituted or substituted with up to 4 substituents independently selected from $R^4$.

EMBODIMENT G

A compound of Formula 1 having the structure of Formula 1-3

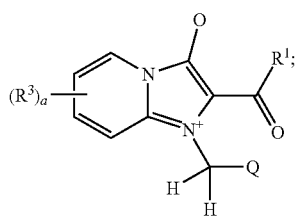

1-3 wherein $R^3$ is F, Cl or $CH_3$, and a is 0 or 1;
$R^1$ is phenyl or pyridinyl, each unsubstituted or substituted with up to 4 substituents independently selected from $R^4$;
Q is

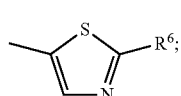

Q-1 and
$R^6$ is $C_1$.

EMBODIMENT G1

A compound of Embodiment G wherein $R^1$ is phenyl, unsubstituted or substituted with up to 4 substituents independently selected from $R^4$.

EMBODIMENT H

A compound of Formula 1 having the structure of Formula 1-5

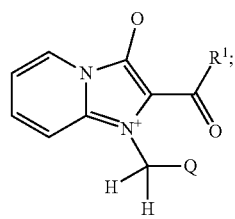

1-5 wherein $R^1$ is phenyl or pyridinyl, each unsubstituted or substituted with up to 4 substituents independently selected from $R^4$;
each $R^4$ is independently $C_1$-$C_4$ alkyl, $C_1$-$C_4$ alkoxy or $C_1$-$C_4$ alkylthio, each unsubstituted or substituted with halogen;
Q is

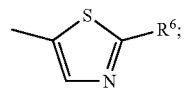

Q-1 and
$R^6$ is $C_1$.

EMBODIMENT H1

A compound of Embodiment H wherein $R^1$ is phenyl, unsubstituted or substituted with up to 4 substituents independently selected from $R^4$.

EMBODIMENT J

A compound of Formula 1 having the structure of Formula 1-1

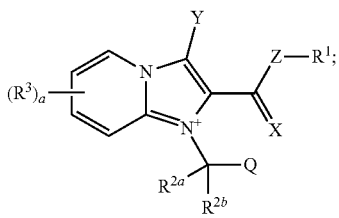

1-1 wherein a is 0, 1, 2 or 3.

EMBODIMENT J1

A compound of Embodiment J wherein
X and Y are O;
$R^{2a}$ and $R^{2b}$ are H.

EMBODIMENT J2

A compound of Embodiment J1 wherein
Z is a direct bond; and
$R^1$ is phenyl or pyridinyl, each unsubstituted or substituted with up to 4 substituents independently selected from $R^4$.

EMBODIMENT J3

A compound of Embodiment J2 wherein
Q is

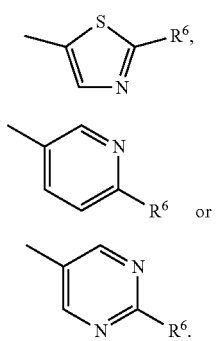

EMBODIMENT J4

A compound of Embodiment J3 wherein
$R^1$ is phenyl, unsubstituted or substituted with up to 4 substituents independently selected from $R^4$;
$R^3$ is F, Cl or $CH_3$;
a is 0 or 1; and
$R^6$ is H, F, Cl, Br, $CH_3$, $CHF_2$ or $CF_3$.

Specific embodiments include compounds of Formula 1 selected from the group consisting of compounds 1, 3, 5, 6, 16, 25, 27, 28 and 29. Further specific embodiments include compounds of Formula 1 selected from the group consisting of compounds 1, 3, 5, 6, 7, 16, 21, 25, 27, 28, 29, 43, 46, 47, 48, 50, 57, 58, 61, 62, 63 and 81. Further specific embodiments include compounds of Formula 1 selected from the group consisting of compounds 3, 6, 25, 48, 57, 72, 76, 92, 94, 98, 121 and 127. Compound numbers refer to Index Table A.

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent. Embodiments of the invention further include methods for controlling an invertebrate pest comprising contacting the invertebrate pest or its environment with a biologically effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a biologically effective amount of a compound of any of the preceding Embodiments and a propellant. Embodiments of the invention further include a bait composition for controlling an invertebrate pest comprising a biologically effective amount of a compound of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include methods for protecting a seed from an invertebrate pest comprising contacting the seed with a biologically effective amount of a compound of any of the preceding Embodiments.

Embodiments of the invention also include methods for protecting an animal from an invertebrate parasitic pest comprising administering to the animal a parasiticidally effective amount of a compound of any of the preceding Embodiments.

Embodiments of the invention also include methods for controlling an invertebrate pest comprising contacting the invertebrate pest or its environment with a biologically effective amount of a compound of Formula 1, an N-oxide or a salt thereof, (e.g., as a composition described herein), provided that the methods are not methods of medical treatment of a human or animal body by therapy.

This invention also relates to such methods wherein the invertebrate pest or its environment is contacted with a composition comprising a biologically effective amount of a compound of Formula 1, an N-oxide or a salt thereof and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

The compounds of Formula 1 can be prepared by one or more of the following methods and variations as described in Schemes 1-4. The definitions of substituents in the compounds of Formulae 1-7 below are as defined above in the Summary of the Invention unless otherwise noted. Compounds of Formulae 1a are subsets of the compounds of Formula 1, and all substituents for Formulae 1a are as defined above for Formula 1. The following abbreviations may be used: DMF is N,N-dimethylformamide, and DBU is 1,8-diazabicyclo[5.4.0]undec-7-ene.

Compounds of Formula 1a (compounds of Formula 1 wherein X and Y are O) can be prepared from compounds of Formula 2 by the method shown in Scheme 1. In this method, a compound of Formula 2 is treated with an acid chloride of Formula 3a or an acid anhydride of Formula 3b in the presence of a base, and the resulting reaction mixture may be optionally heated. Typical reaction solvents include acetonitrile, dichloromethane, ethyl acetate, toluene, dichloroethane, tetrahydrofuran and DMF. Typical reaction temperatures range from 25° C. to 100° C. Typical bases useful in this step include cesium carbonate, potassium carbonate, DBU, N,N-diisopropylethylamine and triethylamine.

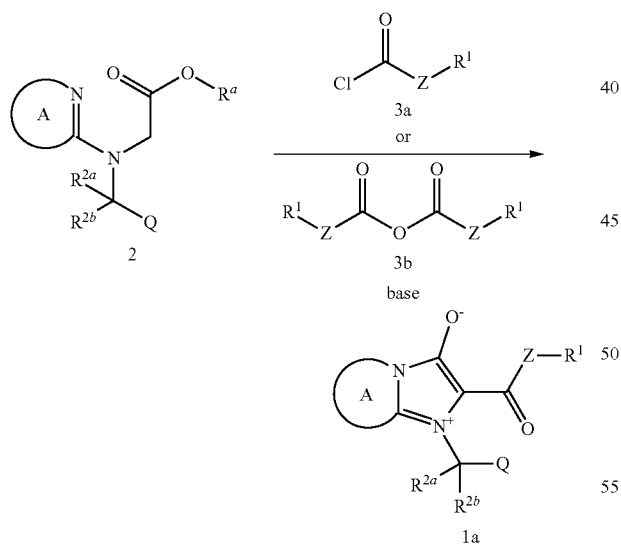

Scheme 1

$R^a$ is $C_1$-$C_4$ alkyl

Compounds of Formula 1a (compounds of Formula 1 wherein X and Y are 0) can also be prepared from compounds of Formula 2 by the two-step method shown in Scheme 2. In this method, a compound of Formula 2a is prepared by either acidic or basic hydrolysis of a compound of Formula 2. In the case of basic hydrolysis, typical bases include alkali metal or tetraalkylammonium hydroxides, and typical solvents include water, methanol, ethanol and isopropanol or mixtures thereof. Typical reaction temperatures range from 0 C to the reflux temperature of the reaction solvent. In the case of acidic hydrolysis, typical solvents include protic solvents such as water, methanol or ethanol, or aprotic solvents such as tetrahydrofuran, dichloromethane or dichloroethane. Typical acids include trifluoroacetic acid or hydrochloric acid. Typical reaction temperatures range from −20° C. to the reflux temperature of the reaction solvent. The compound of Formula 1a is then prepared from the compound of Formula 2a by the method described in Scheme 1.

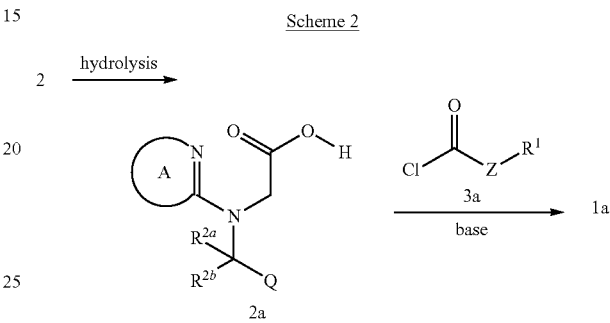

Scheme 2

Compounds of Formula 2 can be prepared from compounds of Formula 4 by the method shown in Scheme 3. In this method, a compound of Formula 4 is alkylated by treatment with Q-C($R^{2a}$)($R^{2b}$)X (Formula 5) wherein X is a leaving group such as chloro, bromo, iodo or sulfonate in the presence of a base. Typical reaction solvents include acetonitrile, dichloromethane, ethyl acetate, tetrahydrofuran, dichloroethane, ethanol, isopropanol and DMF. Typical reaction temperatures range from 25° C. to 100° C. Typical bases useful in this step include sodium hydride, cesium carbonate, potassium carbonate, DBU, N,N-diisopropylethylamine and triethylamine.

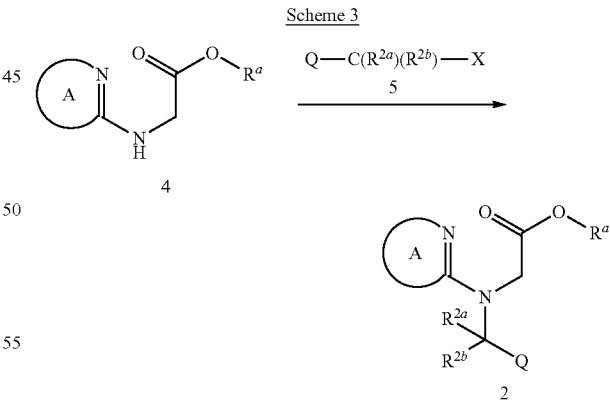

Scheme 3

$R^a$ is $C_1$-$C_4$ alkyl

Compounds of Formula 4 can be prepared from compounds of Formula 7 by the two-step method shown in Scheme 3. In the first step of this method, a compound of Formula 7 is treated with a $C_1$-$C_4$ alkyl chloro- or bromoacetate in the presence of a base to yield the compound of Formula 6. Typical reaction solvents include acetonitrile, dichloromethane, ethyl acetate, dichloroethane, tetrahydrofuran DMF; typical reaction temperatures range from −30° C. to 50° C. Typical bases useful in this step include sodium hydride, cesium carbonate, potassium carbonate, DBU, N,N-diisopropylethylamine and triethylamine. In the second step of this method, the acetate protecting group of the compound of Formula 6 is removed either by acidic or basic hydrolysis to yield the compounds of Formula 4.

Scheme 4

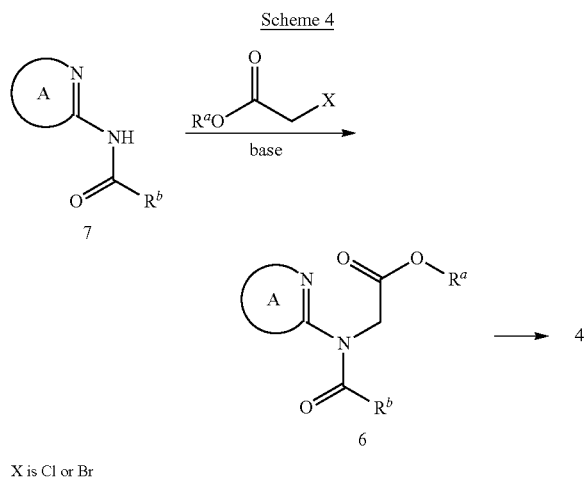

X is Cl or Br
R$^a$ is C$_1$-C$_4$ alkyl
R$^b$ is H or C$_1$-C$_4$ alkyl

Compounds of Formula 1 wherein X or Y is S can be prepared from compounds of Formula 1a by treatment with a thionating reagent such as P$_4$S$_{10}$ or Lawessen's Reagent (2,4-bis(4-methoxyphenyl)-1,3-dithia-2,4-diphosphetane 2,4-disulfide).

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after introduction of the reagents depicted in the individual schemes, additional routine synthetic steps not described in detail may be needed to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. 1H NM R spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet. DMF means N,N-dimethylformamide. Compound numbers refer to Index Table A.

SYNTHESIS EXAMPLE 1

Preparation of 2-benzoyl-1-[(2-chloro-5-thiazolyl) methyl]-3-hydroxyimidazo[1,2-a]pyridinium Inner Salt (compound 1)

Step A: Preparation of N-formyl-N-2-pyridinylglycine methyl ester

N-2-pyridinylformamide (9.7 g, 0.1 mol) was dissolved in anhydrous DMF (100 mL) and cooled in an ice water bath. Sodium hydride (60% dispersion in mineral oil, 6.0 g, 0.15 mol) was added portionwise; after the addition was complete, the reaction mixture was stirred with continued cooling for 10 minutes. Methyl bromoacetate (14.1 mL, 22.8 g, 0.15 mol) was added dropwise, and the reaction mixture was then stirred for 30 minutes with ice bath cooling. The reaction mixture was then quenched carefully with saturated aqueous ammonium chloride solution, and extracted with ethyl acetate. The organic layer was separated, washed with brine, dried (magnesium sulfate) and concentrated to a colorless oil (12.5 g) which was used in the next step without further purification.

Step B: Preparation of N-2-pyridinylglycine methyl ester

N-formyl-N-2-pyridinylglycine methyl ester (5.5 g, 28.4 mmol) was dissolved in a solution of 2.75 mL concentrated hydrochloric acid and 30 mL methanol and stirred overnight at ambient temperature. The reaction mixture was then concentrated and partitioned between saturated aqueous sodium bicarbonate solution and ethyl acetate. The organic layer was separated, dried (magnesium sulfate), and concentrated to yield 4.2 g of the title compound. $^1$H NMR (400 MHz, CDCl$_3$) δ ppm 8.14 (d, 1H), 7.42 (t, 1H), 6.61 (t, 1H), 6.49 (d, 1H), 5.06 (br s, 1H), 4.21 (d, 2H), 3.77 (s, 3H).

Step C: Preparation of N-[(2-chlorothiazol-5-yl) methyl]-N-2-pyridinylglycine methyl Ester N-2-pyridinylglycine methyl ester (1.65 g, 10 mmol), 2-chloro-5-(chloromethyl)thiazole (2.52 g, 15 mmol), tetrabutylammonium iodide (0.37 g, 1 mmol) and N-ethyl-N-isopropylpropan-2-amine (2.6 g, 3.4 mL, 20 mmol) were dissolved in dry acetonitrile (15 mL) and heated at 80° C. overnight. The reaction mixture was then chromatographed on silica gel using a gradient of 0-100% ethyl acetate in hexanes to yield 1.1 g of the title compound. 1H NMR (400 MHz, CDCl$_3$) δ ppm 8.22 (d, 1H), 7.52 (t, 1H), 7.45 (s, 1H), 6.72 (t, 1H), 6.56 (d, 1H), 4.91 (s, 2H), 4.22 (s, 2H), 3.74 (s, 3H).

Step D: Preparation of 2-benzoyl-1-[(2-chloro-5-thiazolyl)methyl]-3-hydroxyimidazo[1,2-a]pyridinium Inner Salt N-[(2-chlorothiazol-5-yl)methyl]-N-2-pyridinylglycine methyl ester (298 rag, 1 mmol) and finely ground potassium carbonate (165 mg, 1.2 mmol) were added to acetonitrile (20 mL), followed by the addition of benzoyl chloride (0.35 mL, 0.42 g, 3 mmol), and the reaction mixture was heated at 80° C. overnight. A further portion of benzoyl chloride (0.35 mL, 0.42 g, 3 mmol) was added, and heating was continued overnight. The reaction mixture was then cooled, filtered, concentrated, and the resulting residue was chromatographed on silica gel using a gradient of 0-100% ethyl acetate in hexanes to yield 110 mg of the title compound, a compound of this invention. $^1$H NMR (400 MHz, CDCl$_3$) δ ppm 8.41 (d, 1H), 7.92 (m, 2H), 7.72 (t, 11H), 7.64 (s, 11H), 7.52 (t, 1H), 7.46-7.48 (m, 3H), 7.01 (t, 1H), 5.92 (s, 2H).

Specific compounds of Formula 1, prepared by the methods and variations as described in preceding Schemes 1-4 and Synthesis Example 1, are shown in the Index Table below. The following abbreviations may be used: Cmpd means Compound, t is tertiary, c is cyclo, Me is methyl, Et is ethyl and Ph is phenyl. The abbreviation "Ex." stands for "Example" and is followed by a number indicating in which Synthesis Example the compound is prepared. For mass spectral data (AP$^+$ (M+1)), the numerical value reported is the molecular weight of the parent molecular ion (M) formed by addition of H (molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported.

INDEX TABLE A

| Cmpd. No. | R | Z | R$^1$ | Q | MS data |
|---|---|---|---|---|---|
| 1 | — | direct bond | phenyl | 2-chloro-5-thiazolyl | 370.4 |
| 2 | — | direct bond | 3-(trifluoromethyl)phenyl | 2-chloro-5-thiazolyl | 438.4 |
| 3 | — | —CF$_2$— | F | 2-chloro-5-thiazolyl | 362.4 |
| 4 | — | —CH$_2$O— | phenyl | 2-chloro-5-thiazolyl | 400.5 |
| 5 | — | direct bond | 4-(trifluoromethyl)phenyl | 2-chloro-5-thiazolyl | 438.3 |
| 6 | — | —CF$_2$CF$_2$— | F | 2-chloro-5-thiazolyl | 412.2 |
| 7 | — | —CF$_2$CF$_2$CF$_2$CF$_2$— | F | 2-chloro-5-thiazolyl | 512.1 |
| 8 | — | direct bond | 4-(benzyloxy)phenyl | 2-chloro-5-thiazolyl | 476.2 |
| 9 | — | direct bond | 3-(benzyloxy)phenyl | 2-chloro-5-thiazolyl | 476.2 |
| 10 | — | —CH$_2$— | phenyl | 2-chloro-5-thiazolyl | 384.3 |
| 11 | — | —CHF— | F | 2-chloro-5-thiazolyl | 344.2 |
| 12 | — | —CF$_2$— | phenyl | 2-chloro-5-thiazolyl | 420.3 |
| 13 | — | —CH$_2$— | 3-(trifluoromethyl)phenyl | 2-chloro-5-thiazolyl | 452.3 |
| 14 | — | —CH$_2$— | 4-(benzyloxy)phenyl | 2-chloro-5-thiazolyl | 490.3 |
| 15 | — | direct bond | 6-chloro-3-pyridinyl | 2-chloro-5-thiazolyl | 405.1 |
| 16 | — | direct bond | 2-methoxy-4-pyridinyl | 2-chloro-5-thiazolyl | 401.3 |
| 17 | — | —CH$_2$— | 4-(trifluoromethyl)phenyl | 2-chloro-5-thiazolyl | 452.2 |
| 18 | — | direct bond | 3-(trifluoromethoxy)phenyl | 2-chloro-5-thiazolyl | 454.2 |
| 19 | — | direct bond | 3,5-dichlorophenyl | 2-chloro-5-thiazolyl | 438.1 |
| 20 | — | direct bond | 3,4-dichlorophenyl | 2-chloro-5-thiazolyl | 438.0 |
| 21 | — | direct bond | 2,4-dichlorophenyl | 2-chloro-5-thiazolyl | 438.1 |
| 22 | — | direct bond | 3-methylphenyl | 2-chloro-5-thiazolyl | 384.2 |
| 21 | — | direct bond | 4-methylphenyl | 2-chloro-5-thiazolyl | 384.2 |
| 24 | — | direct bond | 4-(trifluoromethylthio)phenyl | 2-chloro-5-thiazolyl | 470.2 |
| 25 | — | direct bond | 3-chlorophenyl | 2-chloro-5-thiazolyl | 404.0 |
| 26 | — | direct bond | 4-chlorophenyl | 2-chloro-5-thiazolyl | 404.0 |
| 27 | — | direct bond | 2-fluorophenyl | 2-chloro-5-thiazolyl | 388.1 |
| 28 | — | direct bond | 3-fluorophenyl | 2-chloro-5-thiazolyl | 388.1 |
| 29 | — | direct bond | 4-fluorophenyl | 2-chloro-5-thiazolyl | 388.1 |
| 30 | — | direct bond | 6-chloro-2-pyridinyl | 2-chloro-5-thiazolyl | 406 |
| 31 | — | —O— | phenyl | 2-chloro-5-thiazolyl | 386.0 |
| 32 | — | direct bond | 5-chloro-2-pyridinyl | 2-chloro-5-thiazolyl | 406 |
| 33 | — | direct bond | 3-methoxyphenyl | 2-chloro-5-thiazolyl | 400.1 |
| 34 | — | direct bond | 4-methoxyphenyl | 2-chloro-5-thiazolyl | 400.2 |
| 35 | — | direct bond | 4-(trifluoromethoxy)phenyl | 2-chloro-5-thiazolyl | 454.1 |
| 36 | — | direct bond | 4-(isopentyloxy)phenyl | 2-chloro-5-thiazolyl | 456.2 |
| 37 | — | direct bond | 4-(phenacyloxy)phenyl | 2-chloro-5-thiazolyl | 504.2 |
| 38 | — | direct bond | 2-chloro-3-thienyl | 2-chloro-5-thiazolyl | 411 |
| 39 | — | direct bond | 2-pyridinyl | 2-chloro-5-thiazolyl | 371 |
| 40 | 7-Me | direct bond | phenyl | 2-chloro-5-thiazolyl | 384.1 |
| 41 | 7-Me | direct bond | 3-(trifluoromethyl)phenyl | 2-chloro-5-thiazolyl | 452.1 |
| 42 | — | direct bond | 3-(trifluoromethylthio)phenyl | 2-chloro-5-thiazolyl | 470.2 |
| 43 | — | direct bond | 2,3-difluorophenyl | 2-chloro-5-thiazolyl | 406.2 |
| 44 | — | direct bond | 2,3-difluorophenyl | 2-chloro-5-thiazolyl | 406.2 |
| 45 | — | direct bond | 2,3-difluorophenyl | 2-chloro-5-thiazolyl | 406.2 |
| 46 | — | direct bond | 2,6-difluorophenyl | 2-chloro-5-thiazolyl | 406.2 |

INDEX TABLE A-continued

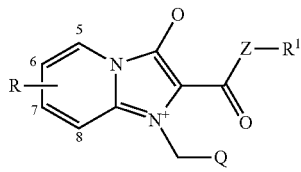

| Cmpd. No. | R | Z | R¹ | Q | MS data |
|---|---|---|---|---|---|
| 47 | — | direct bond | 3,5-difluorophenyl | 2-chloro-5-thiazolyl | 406.2 |
| 48 | — | direct bond | 2,4,6-trifluorophenyl | 2-chloro-5-thiazolyl | 424.1 |
| 49 | — | direct bond | 4-fluoro-3-methoxyphenyl | 2-chloro-5-thiazolyl | 418.2 |
| 50 | — | direct bond | 2-fluoro-3-methoxyphenyl | 2-chloro-5-thiazolyl | 418.2 |
| 51 | — | direct bond | 3,5-dimethoxyphenyl | 2-chloro-5-thiazolyl | 430.2 |
| 52 | — | direct bond | 3-phenoxyphenyl | 2-chloro-5-thiazolyl | 462.2 |
| 53 | — | direct bond | 4-phenoxyphenyl | 2-chloro-5-thiazolyl | 462.3 |
| 54 | — | direct bond | 3-(2-methoxy-2-oxoethyl)phenyl | 2-chloro-5-thiazolyl | 442.3 |
| 55 | — | direct bond | 3-bromo-5-fluorophenyl | 2-chloro-5-thiazolyl | 466.1 |
| 56 | — | direct bond | 2-fluoro-5-(trifluoromethoxy)phenyl | 2-chloro-5-thiazolyl | 472.2 |
| 57 | — | direct bond | 4-bromo-2-chlorophenyl | 2-chloro-5-thiazolyl | 482.1 |
| 58 | — | direct bond | 3-fluoro-5-(trifluoromethoxy)phenyl | 2-chloro-5-thiazolyl | 471.2 |
| 59 | — | direct bond | 3-[[[2-(trifluoromethyl)-4-pyridinyl]oxy]phenyl | 2-chloro-5-thiazolyl | 531.4 |
| 60 | — | direct bond | 4-(2-phenylethoxy)phenyl | 2-chloro-5-thiazolyl | 490.4 |
| 61 | — | direct bond | 2,3,6-trifluorophenyl | 2-chloro-5-thiazolyl | 424.2 |
| 62 | — | direct bond | 2,6-difluoro-4-methoxyphenyl | 2-chloro-5-thiazolyl | 436.3 |
| 63 | — | direct bond | 4-bromo-2,6-difluorophenyl | 2-chloro-5-thiazolyl | 484.2 |
| 64 | — | direct bond | 3-(2-methoxyethoxy)phenyl | 2-chloro-5-thiazolyl | 443.3 |
| 65 | — | direct bond | 3-chloro-5-(trifluoromethoxy)phenyl | 2-chloro-5-thiazolyl | 488.3 |
| 66 | — | direct bond | 5-chloro-2-fluorophenyl | 2-chloro-5-thiazolyl | 422.3 |
| 67 | — | direct bond | 5-bromo-2-methoxyphenyl | 2-chloro-5-thiazolyl | 478.3 |
| 68 | — | direct bond | 4-bromo-2-fluorophenyl | 2-chloro-5-thiazolyl | 466.2 |
| 69 | — | direct bond | 2-chloro-4-fluorophenyl | 2-chloro-5-thiazolyl | 422.3 |
| 70 | — | direct bond | 4-(2-methoxyethoxy)phenyl | 2-chloro-5-thiazolyl | 444.4 |
| 71 | — | direct bond | 4-chloro-2-fluorophenyl | 2-chloro-5-thiazolyl | 422.2 |
| 72 | — | direct bond | 5-bromo-2-fluorophenyl | 2-chloro-5-thiazolyl | 466.2 |
| 73 | — | direct bond | 3-[(6-chloro-3-pyridinyl)methoxy]phenyl | 2-chloro-5-thiazolyl | 511.4 |
| 74 | — | direct bond | 4-(2-methoxy-2-oxo-ethyl)phenyl | 2-chloro-5-thiazolyl | 442.2 |
| 75 | — | direct bond | 2-chloro-6-fluorophenyl | 2-chloro-5-thiazolyl | 422.2 |
| 76 | — | direct bond | 2,5-dimethoxyphenyl | 2-chloro-5-thiazolyl | 430.3 |
| 77 | — | direct bond | 2-chloro-4-cyanophenyl | 2-chloro-5-thiazolyl | 429.3 |
| 78 | — | direct bond | 2,3,4,5-tetrafluorophenyl | 2-chloro-5-thiazolyl | 442.3 |
| 79 | — | direct bond | 2,4,6-trichlorophenyl | 2-chloro-5-thiazolyl | 472.3 |
| 80 | 7-methyl | O | phenyl | 2-chloro-5-thiazolyl | 399.9 |
| 81 | — | direct bond | cyclopropyl | 2-chloro-5-thiazolyl | 333.9 |
| 82 | — | —CH=CH— | phenyl | 2-chloro-5-thiazolyl | 396.9 |
| 83 | — | direct bond | cyclobutyl | 2-chloro-5-thiazolyl | 348.2 |
| 84 | — | —CH$_2$— | Cl | 2-chloro-5-thiazolyl | 341.9 |
| 85 | — | —CH$_2$— | 3-(trifluoromethyl)-1-pyrazolyl | 2-chloro-5-thiazolyl | 442.2 |
| 86 | — | —CH$_2$— | 4-chloro-1-imidazolyl | 2-chloro-5-thiazolyl | 407.9 |
| 87 | — | direct bond | 2-chloro-3-(trifluoromethyl)phenyl | 2-chloro-5-thiazolyl | 472.3 |
| 88 | — | direct bond | 2-chloro-4-(methylsulfonyl)phenyl | 2-chloro-5-thiazolyl | 482.3 |
| 89 | — | direct bond | 2-methyl-4-(trifluoromethyl)-1-thiazolyl | 2-chloro-5-thiazolyl | 459.3 |
| 90 | — | direct bond | 4-cyano-2-methylphenyl | 2-chloro-5-thiazolyl | 409.3 |
| 91 | — | direct bond | 4-cyano-2-fluorophenyl | 2-chloro-5-thiazolyl | 413.3 |
| 92 | — | direct bond | 2-fluoro-4-(trifluoromethyl)phenyl | 2-chloro-5-thiazolyl | 456.3 |
| 93 | — | direct bond | 2,6-difluoro-4-(trifluoromethyl)phenyl | 2-chloro-5-thiazolyl | 474.3 |
| 94 | — | direct bond | 2-naphthalenyl | 2-chloro-5-thiazolyl | 420.2 |
| 95 | — | direct bond | 6-isoquinolinyl | 2-chloro-5-thiazolyl | 421.2 |
| 96 | — | direct bond | 2,4-dichloro-6-fluorophenyl | 2-chloro-5-thiazolyl | 458.3 |
| 97 | — | direct bond | 1-methyl-5-(trifluoromethyl)-4-pyrazolyl | 2-chloro-5-thiazolyl | 442.4 |
| 98 | — | —OCH$_2$CH$_2$— | H | 2-chloro-5-thiazolyl | 338.1 |
| 100 | — | —CH$_2$CH$_2$CF$_2$— | Cl | 2-chloro-5-thiazolyl | 406.1 |

INDEX TABLE A-continued

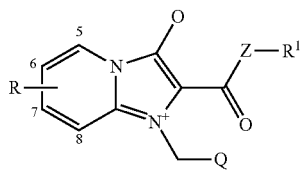

| Cmpd. No. | R | Z | R¹ | Q | MS data |
|---|---|---|---|---|---|
| 101 | — | —CH₂— | 3-chloro-1,2,4-triazol-1-yl | 2-chloro-5-thiazolyl | 409.1 |
| 102 | — | direct bond | 6-quinolinyl | 2-chloro-5-thiazolyl | 421.2 |
| 103 | — | —CH₂NH— | cyclopropyl | 2-chloro-5-thiazolyl | 363.1 |
| 104 | — | direct bond | 3,4-(methylenedioxy)phenyl | 2-chloro-5-thiazolyl | 414.2 |
| 105 | — | direct bond | 3,3-difluorocyclobutyl | 2-chloro-5-thiazolyl | 384 |
| 106 | — | direct bond | 4-bromo-2,2,5,6-tetrafluorophenyl | 2-chloro-5-thiazolyl | 570.3 |
| 107 | — | direct bond | cyclohexyl | 2-chloro-5-thiazolyl | 376.1 |
| 108 | — | direct bond | 3-isoxazolyl | 2-chloro-5-thiazolyl | 361 |
| 109 | — | direct bond | 4-thiazolyl | 2-chloro-5-thiazolyl | 377 |
| 110 | — | —C(O)OCH₂— | H | 2-chloro-5-thiazolyl | 352.1 |
| 111 | — | —C(O)OCH₂CH₂— | H | 2-chloro-5-thiazolyl | 366.1 |
| 112 | — | —O— | 4-chlorophenyl | 2-chloro-5-thiazolyl | 420.1 |
| 113 | — | —OCH₂— | H | 2-chloro-5-thiazolyl | 324.1 |
| 114 | — | direct bond | 2,3-(methylenedioxy)phenyl | 2-chloro-5-thiazolyl | 414.1 |
| 115 | — | direct bond | 2,2-difluoro-1,3-benzodioxol-4-yl | 2-chloro-5-thiazolyl | 450.1 |
| 116 | — | —C(O)NH— | cyclopropyl | 2-chloro-5-thiazolyl | 377 |
| 117 | — | —C(O)— | phenyl | 2-chloro-5-thiazolyl | 398.1 |
| 118 | — | direct bond | 4-cyano-2,6-difluorophenyl | 2-chloro-5-thiazolyl | 431.1 |
| 119 | — | direct bond | 4-cyano-2,6-difluorophenyl | 2-bromo-5-thiazolyl | 475.4 |
| 120 | — | direct bond | 4-cyano-2-fluorophenyl | 2-bromo-5-thiazolyl | 457.4 |
| 121 | — | direct bond | 3-chloro-2-fluoro-5-(trifluoromethyl)phenyl | 2-chloro-5-thiazolyl | 490.4 |
| 122 | — | direct bond | 2,4,6-trifluorophenyl | 2-bromo-5-thiazolyl | 468.4 |
| 123 | — | direct bond | 3-bromo-5-chlorophenyl | 2-chloro-5-thiazolyl | 482.3 |
| 124 | — | direct bond | 4-bromo-2,6-dichlorophenyl | 2-chloro-5-thiazolyl | 500.3 |
| 125 | — | direct bond | 3-bromo-4,6-difluorophenyl | 2-chloro-5-thiazolyl | 484.1 |
| 126 | — | direct bond | 1-naphthalenyl | 2-chloro-5-thiazolyl | 428.1 |
| 127 | — | direct bond | 2,3-dihydro-1,4-benzodioxin-5-yl | 2-chloro-5-thiazolyl | 428.1 |
| 128 | — | direct bond | 4-fluoro-1-naphthalenyl | 2-chloro-5-thiazolyl | 438.2 |
| 129 | — | direct bond | 5,6,7,8-tetrahydro-1-naphthalenyl | 2-chloro-5-thiazolyl | 424 |
| 130 | — | direct bond | 2,2-difluoro-1,3-benzodioxol-5-yl | 2-chloro-5-thiazolyl | 450.1 |
| 131 | — | direct bond | 5-benzofuranyl | 2-chloro-5-thiazolyl | 410 |
| 132 | — | —C(O)O— | hydrogen | 2-chloro-5-thiazolyl | 424 |
| 133 | — | —NH— | cyclopropyl | 2-chloro-5-thiazolyl | 292 |
| 134 | — | —O— | hydrogen | 2-chloro-5-thiazolyl | 309.9 |
| 135 | — | —NHCH₂CF₂— | F | 2-chloro-5-thiazolyl | 419 |
| 136 | — | —C(O)NH— | 4-fluorophenyl | 2-chloro-5-thiazolyl | 431 |
| 137 | — | —CH₂— | 3-cyano-1,2,4-triazol-1-yl | 2-chloro-5-thiazolyl | 400.1 |
| 138 | — | —CH₂— | 3-carbomethoxy-1,2,4-triazol-1-yl | 2-chloro-5-thiazolyl | 433.1 |
| 139 | — | —CH₂— | 3-bromo-1,2,4-triazol-1-yl | 2-chloro-5-thiazolyl | 454.9 |
| 140 | — | —CH₂— | 3-methyl-1,2,4-triazol-1-yl | 2-chloro-5-thiazolyl | 389.1 |
| 141 | — | direct bond | 5,6,7,8-tetrahydro-2-naphthalenyl | 2-chloro-5-thiazolyl | 511.9 |
| 142 | — | direct bond | 2,3-dihydro-1,4-benzodioxin-6-yl | 2-chloro-5-thiazolyl | 428 |
| 143 | — | —CH₂— | 4-chloro-1-pyrazolyl | 2-chloro-5-thiazolyl | 408 |
| 144 | — | —CH₂— | 3-carbomethoxy-1-pyrazolyl | 2-chloro-5-thiazolyl | 446.1 |
| 145 | — | —CH₂NH— | phenyl | 2-chloro-5-thiazolyl | 399 |
| 146 | — | —CH₂NH— | 4-fluorophenyl | 2-chloro-5-thiazolyl | 417 |
| 147 | — | —CH₂— | 1,2,4-triazol-1-yl | 2-chloro-5-thiazolyl | 376.1 |
| 148 | — | —CH₂— | 1,2,3-triazol-1-yl | 2-chloro-5-thiazolyl | 375 |
| 149 | — | —CH₂— | 1,2,5-triazol-1-yl | 2-chloro-5-thiazolyl | 374.9 |
| 150 | — | —NH— | 4-fluorophenyl | 2-chloro-5-thiazolyl | 292 |
| 151 | — | direct bond | 3-methoxy-5-(3-methylbutoxy)phenyl | 2-chloro-5-thiazolyl | 486 |
| 152 | — | direct bond | 5-butoxy-3-methoxyphenyl | 2-chloro-5-thiazolyl | 472 |
| 153 | — | direct bond | 3-methoxy-5-(2-phenylethoxy)phenyl | 2-chloro-5-thiazolyl | 520 |
| 154 | — | direct bond | 3-methoxy-5-(2-methylpropoxy)phenyl | 2-chloro-5-thiazolyl | 472 |
| 155 | — | direct bond | 3-methoxy-5-(2-methoxyethoxy)phenyl | 2-chloro-5-thiazolyl | 474 |

INDEX TABLE A-continued

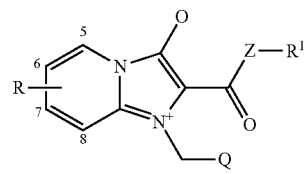

| Cmpd. No. | R | Z | R¹ | Q | MS data |
|---|---|---|---|---|---|
| 156 | — | —C(O)— | 4.-bromo-2,6-difluorophenyl | 2-chloro-5-thiazolyl | 511.9 |
| 157 | — | —C(O)— | 2,4,6-trifluorophenyl | 2-chloro-5-thiazolyl | 452 |
| 158 | — | —C(O)— | 2,6-difluorophenyl | 2-chloro-5-thiazolyl | 433.9 |
| 159 | — | —C(O)— | 6-bromo-2,4-difluorophenyl | 2-chloro-5-thiazolyl | 511.9 |

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil in water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil in water emulsion, flowable concentrate and suspoemulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethylphosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters alkyl and aryl benzoates, γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modem Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, U K, 2000.

In the following Examples, all formulations are prepared in conventional ways. Compound numbers refer to compounds in Index Tables A-G. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

| High Strength Concentrate | |
|---|---|
| Compound 3 | 98.5% |
| silica aerogel | 0.5% |
| synthetic amorphous fine silica | 1.0% |

EXAMPLE B

| Wettable Powder | |
|---|---|
| Compound 6 | 65.0% |
| dodecylphenol polyethylene glycol ether | 2.0% |
| sodium ligninsulfonate | 4.0% |

-continued

| Wettable Powder | |
|---|---|
| sodium silicoaluminate | 6.0% |
| montmorillonite (calcined) | 23.0% |

EXAMPLE C

| Granule | |
|---|---|
| Compound 25 | 10.0% |
| attapulgite granules (low volatile matter, 0.71/0.30 mm; U.S.S. No. 25-50 sieves) | 90.0% |

EXAMPLE D

| Extruded Pellet | |
|---|---|
| Compound 48 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

| Emulsifiable Concentrate | |
|---|---|
| Compound 57 | 10.0% |
| polyoxyethylene sorbitol hexoleate | 20.0% |
| $C_6$-$C_{10}$ fatty acid methyl ester | 70.0% |

EXAMPLE F

| Microemulsion | |
|---|---|
| Compound 72 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

| Seed Treatment | |
|---|---|
| Compound 76 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

EXAMPLE H

| Fertilizer Stick | |
|---|---|
| Compound 92 | 2.5% |
| pyrrolidone-styrene copolymer | 4.8% |
| tristyrylphenyl 16-ethoxylate | 2.3% |
| talc | 0.8% |
| corn starch | 5.0% |
| slow-release fertilizer | 36.0% |
| kaolin | 38.0% |
| water | 10.6% |

EXAMPLE I

| Suspension Concentrate | |
|---|---|
| compound 94 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

EXAMPLE J

| Emulsion in Water | |
|---|---|
| compound 98 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

EXAMPLE K

| Oil Dispersion | |
|---|---|
| compound 121 | 25% |
| polyoxyethylene sorbitol hexaoleate | 15% |
| organically modified bentonite clay | 2.5% |
| fatty acid methyl ester | 57.5% |

EXAMPLE L

| Suspoemulsion | |
|---|---|
| compound 127 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, INVICTA RR2 PRO™, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

Nonagronomic uses of the present compounds and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of the present invention are suitable for systemic and/or non-systemic control of infestation or infection by parasites on animals. Compounds and compositions of the present invention are particularly suitable for combating external parasitic or disease transmitting pests. Compounds and compositions of the present invention are suitable for combating parasites that infest agricultural working animals, such as cattle, sheep, goats, horses, pigs, donkeys, camels, buffalos, rabbits, hens, turkeys, ducks, geese and bees; pet animals and domestic animals such as dogs, cats, pet birds and aquarium fish; as well as so-called experimental animals, such as hamsters, guinea pigs, rats and mice. By combating these parasites, fatalities and performance reduction (in terms of meat, milk, wool, skins, eggs, honey, etc.) are reduced, so that applying a composition comprising a compound of the present invention allows more economic and simple husbandry of animals.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera frugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocrocis medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), striped riceborer (*Chilo suppressalis* Walker), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eujiala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brown-banded cockroach (*Supella longipalpa* Fabricius), American cockroach (*Periplaneta americana* Linnaeus), brown cockroach (*Periplaneta brunnea* Bunnrmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus vestitus*), Denver billbug (*Sphenophorus cicatristriatus* Fahraeus)); flea beetles, cucumber beetles, rootworms, leaf beetles, potato beetles, and leafininers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/ June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Fofficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rarnbur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capilis* De Geer), body louse (*Pediculus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (*Prostephanus truncatus*), lesser grain borer (*Rhyzopertha dominica*), rice weevil (*Stiophilus oryzae*), maize weevil (*Stiophilus zeamais*), cowpea weevil (*Callosobruchus maculatus*), red flour beetle (*Tribolium castaneum*), granary weevil (*Stiophilus granarius*), Indian meal moth (*Plodia interpunctella*), Mediterranean flour beetle (*Ephestia kuhniella*) and flat or rusty grain beetle (*Cyptolestis fernrugineus*).

Compounds of the present invention may have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention may have activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffenrmüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecoia* Patch (spirea aphid), *Aulacorthum solani* Kaltenbach (foxglove aphid), *Chaetosiphon fragaefolii* Cockerell (strawberry aphid), *Diuraphis noxia* Kurdjumnov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocvba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schiffer (cotton stainer), *Euchistus servus* Say (brown stink bug), *Euchistus variolarius* Palisot de Beauvois (one-spotted stink bug), *Graptosthetus* spp. (complex of seed bugs), *Halymorpha halys* Stål (brown marmorated stink bug), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips)); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Note that some contemporary classification systems place Homoptera as a suborder within the order Hemiptera.

Of note is use of compounds of this invention for controlling western flower thrips (*Frankliniella occidentalis*). Of note is use of compounds of this invention for controlling potato leafhopper (*Empoasca fabae*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling sweetpotato whitefly (*Bemisia tabaci*).

Compounds of the present invention may also be useful for increasing vigor of a crop plant. This method comprises contacting the crop plant (e.g., foliage, flowers, fruit or roots) or the seed from which the crop plant is grown with a compound of Formula 1 in amount sufficient to achieve the desired plant vigor effect (i.e. biologically effective amount). Typically the compound of Formula 1 is applied in a formulated composition. Although the compound of Formula 1 is often applied directly to the crop plant or its seed, it can also be applied to the locus of the crop plant, i.e. the environment of the crop plant, particularly the portion of the environment in close enough proximity to allow the compound of Formula 1 to migrate to the crop plant. The locus relevant to this method most commonly comprises the growth medium (i.e. medium providing nutrients to the plant), typically soil in which the plant is grown. Treatment of a crop plant to increase vigor of the crop plant thus comprises contacting the crop plant, the seed from which the crop plant is grown or the locus of the crop plant with a biologically effective amount of a compound of Formula 1.

Increased crop vigor can result in one or more of the following observed effects: (a) optimal crop establishment as demonstrated by excellent seed germination, crop emergence and crop stand; (b) enhanced crop growth as demonstrated by rapid and robust leaf growth (e.g., measured by leaf area index), plant height, number of tillers (e.g., for rice), root mass and overall dry weight of vegetative mass of the crop; (c) improved crop yields, as demonstrated by time to flowering, duration of flowering, number of flowers, total biomass accumulation (i.e. yield quantity) and/or fruit or grain grade marketability of produce (i.e. yield quality); (d) enhanced ability of the crop to withstand or prevent plant disease infections and arthropod, nematode or mollusk pest infestations; and (e) increased ability of the crop to withstand environmental stresses such as exposure to thermal extremes, suboptimal moisture or phytotoxic chemicals.

The compounds of the present invention may increase the vigor of treated plants compared to untreated plants by killing or otherwise preventing feeding of phytophagous invertebrate pests in the environment of the plants. In the absence of such control of phytophagous invertebrate pests, the pests reduce plant vigor by consuming plant tissues or sap, or transmitting plant pathogens such as viruses. Even in the absence of phytophagous invertebrate pests, the compounds of the invention may increase plant vigor by modifying metabolism of plants. Generally, the vigor of a crop plant will be most significantly increased by treating the plant with a compound of the invention if the plant is grown in a nonideal environment, i.e. an environment comprising one or more aspects adverse to the plant achieving the fill genetic potential it would exhibit in an ideal environment.

Of note is a method for increasing vigor of a crop plant wherein the crop plant is grown in an environment comprising phytophagous invertebrate pests. Also of note is a method for increasing vigor of a crop plant wherein the crop plant is grown in an environment not comprising phytophagous invertebrate pests. Also of note is a method for increasing vigor of a crop plant wherein the crop plant is grown in an environment comprising an amount of moisture less than ideal for supporting growth of the crop plant. Of note is a method for increasing vigor of a crop plant wherein the crop is rice. Also of note is a method for increasing vigor of a crop plant wherein the crop is maize (corn). Also of note is a method for increasing vigor of a crop plant wherein the crop is soybean.

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, at least one additional component selected from the group consisting of surfactants, solid diluents and liquid diluents, and at least one additional biologically active compound or agent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-1-oxo-9-(3-pyridinyl)-2H,11H-naphtho[2,1-b]pyrano[3,4-e]pyran-4-yl]methyl cyclopropanecarboxylate), amidoflumet, amitraz, avermectin, azadirachtin, azinphos-methyl, benfuracarb, bensultap, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(-cyclopropylethyl)amino]carbonyl]phenyl]-1-(3-chloro-2-pyridinyl)-1H-pyrazole-5-carboxamide), cyclprothrin, cycloxaprid ((5S,8R)-1-[(6-chloro-3-pyridinyl)methyl]-2,3,5,6,7,8-hexahydro-9-nitro-5,8-Epoxy-1H-imidazo[1,2-a]azepine) cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin (2-ethyl-3,7-dimethyl-6-[4-(trifluoromethoxy)phenoxy]-4-quinolinyl methyl carbonate), flonicamid, flubendiamide, flucythrinate, flufenerim, flufenoxuron, flufenoxystrobin (methyl (αE)-2-[[2-chloro-4-(trifluoromethyl)phenoxy]methyl]-α-(methoxymethylene)benzeneacetate), flufensulfone (5-chloro-2-[(3,4,4-trifluoro-3-buten-1-yl)sulfonyl]thiazole), fluhexafon, fluopyram, flupiprole (1-[2,6-dichloro-4-(trifluoromethyl)phenyl]-5-[(2-ethyl-2-propen-1-yl)amino]-4-[(trifluoromethyl)sulfinyl]-1H-pyrazole-3-carbonitrile), flupyradifurone (4-[[(6-chloro-3-pyridinyl)methyl](2,2-difluoroethyl)amino]-2(5H)-furanone), fluvalinate, tau-fluvalinate, fonophos, formetanate, fosthiazate, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hexythiazox, hydramethylnon, imidacloprid, indoxacarb, insecticidal soaps, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methiodicarb, methomyl, methoprene, methoxychlor, metofluthrin, methoxyfenozide, metofluthrin, monocrotophos, monofluorothrin ([2,3,5,6-tetrafluoro-4-(methoxymethyl)phenyl]methyl 3-(2-cyano-1-propen-1-yl)-2,2-dimethylcyclopropanecarboxylate), nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), pymetrozine, pyrafluprole, pyrethrin, pyridaben, pyridalyl, pyrifluquinazon, pyriminostrobin (methyl (E)-2-[[[2-[(2,4-dichlorophenyl)amino]-6-(trifluoromethyl)-4-pyrimidinyl]oxy]methyl]-C-(methoxymethylene)benzenzeneacetate), pyriprole, pyriproxyfen, rotenone, ryanodine, silafluofen, spinetoram, spinosad, spirodiclofen, spiromesifen, spirotetramat, sulprofos, sulfoxaflor (N-[methyloxido[1-[6-(trifluoromethyl)-3-pyridinyl]ethyl]-$\lambda^4$-sulfanylidene]cyanamide), tebufenozide, tebufenpyrad, teflubenzuron, tefluthrin, terbufos, tetrachlorvinphos, tetramethrin, tetramethylfluthrin ([2,3,5,6-tetrafluoro-4-(methoxymethyl)phenyl]methyl 2,2,3,3-tetramethylcyclopropanecarboxylate), tetraniliprole, thiacloprid, thiamethoxam, thiodicarb, thiosultap-sodium, tioxazafen (3-phenyl-5-(2-thienyl)-1,2,4-oxadiazole), tolfenpyrad, tralomethrin, triazamate, trichlorfon, triflumezopyrim (2,4-dioxo-1-(5-pyrimidinylmethyl)-3-[3-(trifluoromethyl)phenyl]-2H-pyrido[1,2-a]pyrimidinium inner salt), triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, afidopyropen, amitraz, avermectin, azadirachtin, benfuracarb, bensultap, bifenthrin, buprofezin, cadusafos, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, flufensulfone, flupiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiodicarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, *Bacillus thuringiensis* delta-endotoxins, all strains of *Bacillus thuringiensis* and all strains of nucleo polyhedrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, acetylcholinesterase (AChE) inhibitors such as the carbamates methomyl, oxamyl, thiodicarb, triazamate, and the organophosphates chlorpyrifos; GABA-gated chloride channel antagonists such as the cyclodienes dieldrin and endosulfan, and the phenylpyrazoles ethiprole and fipronil; sodium channel modulators such as the pyrethroids bifenthrin, cyfluthrin, beta-cyfluthrin, cyhalothrin, lambda-cyhalothrin, cypermethrin, deltamethrin, dimefluthrin, esfenvalerate, metofluthrin and profluthrin; nicotinic acetylcholinereceptor (nAChR) agonists such as the neonicotinoids acetamiprid, clothianidin, dinotefuran, imidacloprid, nitenpyram, nithiazine, thiacloprid, and thiamethoxam, and sulfoxaflor; nicotinic acetylcholine receptor (nAChR) allosteric activators such as the spinosyns spinetoram and spinosad; chloride channel activators such as the avermectins abamectin and emamectin; juvenile hormone mimics such as diofenolan, methoprene, fenoxycarb and pyriproxyfen; selective homopteran feeding blockers such as pymetrozine and flonicamid; mite growth inhibitors such as etoxazole; inhibitors of mitochondrial ATP synthase such as propargite; ucouplers of oxidative phosphorylation via disruption of the proton gradient such as chlorfenapyr; nicotinic acetylcholine receptor (nAChR) channel blockers such as the nereistoxin analogs cartap; inhibitors of chitin biosynthesis such as the benzoylureas flufenoxuron, hexaflumuron, lufenuron, novaluron, noviflumuron and triflumuron, and buprofezin; dipteran moulting disrupters such as cyromazine; ecdysone receptor agonists such as the diacylhydrazines methoxyfenozide and tebufenozide; octopamine receptor agonists such as amitraz; mitochondrial complex III electron transport inhibitors such as hydramethylnon; mitochondrial complex I electron transport inhibitors such as pyridaben; voltage-dependent sodium channel blockers such as indoxacarb; inhibitors of acetyl CoA carboxylase such as the tetronic and tetramic acids spirodiclofen, spiromesifen and spirotetramat; mitochondrial complex II electron transport inhibitors such as the 1-ketonitriles cyenopyrafen and cyflumetofen; ryanidine receptor modulators such as the anthranilic diamides chlorantraniliprole, cyantraniliprole and cyantraniliprole, diamides such as flubendiamide, and ryanodine receptor ligands such as ryanodine; compounds wherein the target site responsible for biological activity is unknown or uncharacterized such as azadirachtin, bifenazate, pyridalyl, pyrifluquinazon and triflumezopyrim; microbial disrupters of insect midgut membranes such as *Bacillus thuringensis* and the delta-endotoxins they produce and *Bacillus sphaericus*; and biological agents including nucleo polyhedro viruses (NPV) and other naturally occurring or genetically modified insecticidal viruses.

Further examples of biologically active compounds or agents with which compounds of this invention can be formulated are: fungicides such as acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, etaconazole, edifenphos, enoxastrobin (also known as enestroburin), epoxiconazole, ethaboxam, ethirimol, etridiazole, famoxadone, fenamidone, fenaminstrobin, fenarimol, fenbuconazole, fenfuram, fenhexamide, fenoxanil, fenpiclonil, fenpropidin, fenpropimorph, fenpyrazamine, fentin acetate, fentin hydroxide, ferbam, ferimzone, flometoquin, fluazinam, fludioxonil, flufenoxystrobin, flumorph, fluopicolide, fluopyram, fluoxastrobin, fluquinconazole, flusilazole, flusulfamide, flutianil, flutolanil, flutriafol, fluxapyroxad, folpet, fthalide (also known as phthalide), fuberidazole, furalaxyl, furametpyr, hexaconazole, hymexazole, guazatine, imazalil, imibenconazole, iminoctadine albesilate, iminoctadine triacetate, iodicarb, ipconazole, isofetamid, iprobenfos, iprodione, iprovalicarb, isoprothiolane, isopyrazam, isotianil, kasugamycin, kresoximmethyl, mancozeb, mandipropamid, mandestrobin, maneb, mapanipyrin, mepronil, meptyldinocap, metalaxyl (including metalaxyl-M/mefenoxam), metconazole, methasulfocarb, metiram, metominostrobin, metrafenone, myclobutanil, naffitine, neo-asozin (ferric methanearsonate), nuarimol, octhilinone, ofurace, orysastrobin, oxadixyl, oxathiapiprolin, oxolinic acid, oxpoconazole, oxycarboxin, oxytetracycline, penconazole, pencycuron, penflufen, penthiopyrad, perfurazoate, phosphorous acid (including salts thereof, e.g., fosetyl-aluminm), picoxystrobin, piperalin, polyoxin, probenazole, prochloraz, procymidone, propamocarb, propiconazole, propineb, proquinazid, prothiocarb, prothioconazole, pyraclostrobin, pyrametostrobin, pyraoxystrobin, pyrazophos, pyribencarb, pyributacarb, pyrifenox, pyriofenone, perisoxazole, pyrimethanil, pyrifenox, pyrrolnitrin, pyroquilon, quinconazole, quinmethionate, quinoxyfen, quintozene, silthiofam, sedaxane, simeconazole, spiroxamine, streptomycin, sulfur, tebuconazole, tebufloquin, tecloffhalam, tecloftalam, tecnazene, terbinafine, tetraconazole, thiabendazole, thifluzamide, thiophanate, thiophanate-methyl, thiram, tiadinil, tolciofos-methyl, tolprocarb, tolyfluanid, triadimefon, triadimenol, triarimol, triazoxide, tribasic copper sulfate, triclopyricarb, tridemorph, trifloxystrobin, triflumizole, trimoprhamide tricyclazole, trifloxystrobin, triforine, triticonazole, uniconazole, validamycin, valifenalate (also known as valifenal), vinclozolin, zineb, ziram, zoxamide and 1-[4-[4-[5-(2,6-difluorophenyl)-4,5-dihydro-3-isoxazolyl]-2-thiazolyl]-1-piperidinyl]-2-[5-methyl-3-(trifluoromethyl)-1-pyrazol-1-yl]ethanone; nematocides such as fluopyram, spirotetramat, thiodicarb, fosthiazate, abamectin, iprodione, fluensulfone, dimethyl disulfide, tioxazafen, 1,3-dichloropropene (1,3-D), metam (sodium and potassium), dazomet, chloropicrin, fenamiphos, ethoprophos, cadusaphos, terbufos, imicyafos, oxamyl, carbofuran, tioxazafen, *Bacillus firmus* and *Pasteuria nishizawae*; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of the invention are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant and seed cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants and seeds can be genetically modified to exhibit traits of, for example, herbicide tolerance, insect-resistance, modified oil profiles or drought tolerance.

Treatment of genetically modified plants and seeds with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants and seeds.

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with compounds of this invention can also increase vigor of plants growing from the seed.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide or salt thereof and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

Compounds of Formula 1 and their compositions, both alone and in combination with other insecticides, nematicides, and fungicides, are particularly useful in seed treatment for crops including, but not limited to, maize or corn, soybeans, cotton, cereal (e.g., wheat, oats, barley, rye and rice), potatoes, vegetables and oilseed rape.

Other insecticides with which compounds of Formula 1 can be formulated to provide mixtures useful in seed treatment include abamectin, acetamiprid, acrinathrin, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetae, formtanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhedrosis* viruses.

Fungicides with which compounds of Formula 1 can be formulated to provide mixtures useful in seed treatment include amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Compositions comprising compounds of Formula 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM 1-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by *rhizobia* bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1, an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

One embodiment of the present invention relates to a method for controlling invertebrate pests, comprising diluting the pesticidal composition of the present invention (a compound of Formula 1 formulated with surfactants, solid diluents and liquid diluents or a formulated mixture of a compound of Formula 1 and at least one other pesticide) with water, and optionally adding an adjuvant to form a diluted composition, and contacting the invertebrate pest or its environment with an effective amount of said diluted composition.

Although a spray composition formed by diluting with water a sufficient concentration of the present pesticidal composition can provide sufficient efficacy for controlling invertebrate pests, separately formulated adjuvant products can also be added to spray tank mixtures. These additional adjuvants are commonly known as "spray adjuvants" or "tank-mix adjuvants", and include any substance mixed in a spray tank to improve the performance of a pesticide or alter the physical properties of the spray mixture. Adjuvants can be surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

Among the spray adjuvants, oils including crop oils, crop oil concentrates, vegetable oil concentrates and methylated seed oil concentrates are most commonly used to improve the efficacy of pesticides, possibly by means of promoting more even and uniform spray deposits. In situations where phytotoxicity potentially caused by oils or other water-immiscible liquids are of concern, spray compositions prepared from the composition of the present invention will generally not contain oil-based spray adjuvants. However, in situations where phytotoxicity caused by oil-based spray adjuvants is commercially insignificant, spray compositions prepared from the composition of the present composition can also contain oil-based spray adjuvants, which can potentially further increase control of invertebrate pests, as well as rainfastness.

Products identified as "crop oil" typically contain 95 to 98% paraffin or naphtha-based petroleum oil and 1 to 2% of one or more surfactants functioning as emulsifiers. Products identified as "crop oil concentrates" typically consist of 80 to 85% of emulsifiable petroleum-based oil and 15 to 20% of nonionic surfactants. Products correctly identified as "vegetable oil concentrates" typically consist of 80 to 85% of vegetable oil (i.e. seed or fruit oil, most commonly from cotton, linseed, soybean or sunflower) and 15 to 20% of nonionic surfactants. Adjuvant performance can be improved by replacing the vegetable oil with methyl esters of fatty acids that are typically derived from vegetable oils. Examples of methylated seed oil concentrates include MSO® Concentrate (UAP-Loveland Products, Inc.) and Premium MSO Methylated Spray Oil (Helena Chemical Company).

The amount of adjuvants added to spray mixtures generally does not exceed about 2.5% by volume, and more typically the amount is from about 0.1 to about 1% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet® (Helena Chemical Company) polyalkyleneoxide modified heptamethyltrisiloxane and Assist® (BASF) 17% surfactant blend in 83% paraffin based mineral oil.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A-G for compound descriptions.

BIOLOGICAL EXAMPLES OF THE INVENTION

Formulation and Spray Methodology for Tests A-G

Test compounds were formulated using a solution containing 10% acetone, 90% water and 300 ppm Activator 90® non-ionic surfactant (Loveland Products, Loveland, Colo., USA). The formulated compounds were applied in 1 mL of liquid through an atomizer nozzle positioned 1.27 cm (0.5 inches) above the top of each test unit. Test compounds were sprayed at the rates indicated, and each test was replicated three times.

Test A

For evaluating control of diamondback moth (*Plutella xylostella* (L.)) the test unit consisted of a small open container with a 12-14-day-old mustard plant inside. This was pre-infested with ~50 neonate larvae that were dispensed into the test unit via corn cob grits using an inoculator. The larvae moved onto the test plant after being dispensed into the test unit.

Test compounds were formulated and sprayed at 250 and/or 50 ppm. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed, and larvae were assessed for mortality.

Of the compounds of Formula 1 tested at 250 ppm, the following provided very good to excellent levels of control efficacy (40% or less feeding damage and/or 100% mortality): 1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 33, 34, 35, 38, 39, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 75, 76, 77, 78, 79, 81, 83, 85, 87, 88, 89, 90, 91, 92, 93, 94, 95, 96, 97, 98, 100, 101, 102, 104, 105, 106, 107, 108, 109, 110, 111, 112, 113, 114, 115,117, 118, 119, 120, 121,122, 123,124, 125, 126, 127, 128, 129, 130, 131,133, 139, 141, 142, 150, 151, 152, 153, 154 and 155.

Of the compounds of Formula 1 tested at 50 ppm, the following provided very good to excellent levels of control efficacy (40% or less feeding damage and/or 100% mortality): 1, 2, 3, 4, 5, 6, 7, 9, 10, 11, 12, 15, 16, 18, 19, 20, 21, 22, 23, 25, 26, 27, 28, 29, 33, 34, 35, 42, 43, 44, 45, 46, 47, 48, 49, 50, 52, 55, 56, 57, 58, 59, 60, 61, 62, 63, 64, 65, 66, 67, 68, 69, 70, 71, 72, 73, 75, 76, 77, 79, 81, 83, 87, 89, 90, 91, 92, 93, 94, 96, 100, 101, 102, 104, 105, 106, 108, 111, 113, 114, 117, 118, 119, 120, 121, 122, 123,124, 125, 126, 127, 128, 129, 130, 131,139, 150 and 151.

Test B

For evaluating control of fall armyworm (*Spodoptera frugiperda* (J. E. Smith)) the test unit consisted of a small open container with a 4-5-day-old corn (maize) plant inside. This was pre-infested with 10-15 1-day-old larvae on a piece of insect diet.

Test compounds were formulated and sprayed at 250 and/or 50 ppm. After spraying of the formulated test compound, the test units were maintained in a growth chamber for 6 days at 25° C. and 70% relative humidity. Plant feeding damage was then visually assessed based on foliage consumed, and larvae were assessed for mortality.

Of the compounds of Formula 1 tested at 250 ppm, the following provided very good to excellent levels of control efficacy (40% or less feeding damage and/or 100% mortality): 2, 3, 5, 6, 7, 8, 11, 15, 18, 19, 21, 23, 24, 25, 26, 27, 28, 29, 33, 34, 35, 42, 43, 46, 47, 48, 50, 53, 55, 56, 57, 58, 61, 62, 63, 65, 66, 67, 68, 71, 72, 77, 81, 87, 90, 91, 92, 93, 94, 95, 96, 100, 104, 106, 114, 118, 119, 120, 121, 122, 123, 124, 126, 127, 128, 130, 131, 151 and 154.

Of the compounds of Formula 1 tested at 50 ppm, the following provided very good to excellent levels of control efficacy (40% or less feeding damage and/or 100% mortality): 5, 7, 8, 21, 25, 48, 57, 62, 63, 65, 72, 92, 93, 94, 96, 120, 121, 122, 123, 124, 130, 151 and 154.

Test C

For evaluating control of corn planthopper (*Peregrinus maidis* (Ashmead)) through contact and/or systemic means, the test unit consisted of a small open container with a 3-4-day-old corn (maize) plant inside. White sand was added to the top of the soil prior to application of the test compound.

Test compounds were formulated and sprayed at 250 and/or 50 ppm. After spraying of the formulated test compound, the test units were allowed to dry for 1 h before they were post-infested with ~15-20 nymphs (18-to-21-day-old). A black, screened cap was placed on the top of each test unit, and the test units were held for 6 days in a growth chamber at 22-24° C. and 50-70% relative humidity. Each test unit was then visually assessed for insect mortality.

Of the compounds of Formula 1 tested at 250 ppm, the following resulted in at least 80% mortality: 1, 3, 4, 6, 7, 10, 15, 16, 18, 21, 22, 25, 27, 28, 29, 30, 32, 33, 43, 44, 45, 46, 47, 48, 50, 56, 57, 58, 61, 66, 67, 72, 75, 81, 90, 98, 104, 110, 111, 113, 114, 117, 118, 120, 122, 125, 127, 133, 135, 139 and 149.

Of the compounds of Formula 1 tested at 50 ppm, the following resulted in at least 80% mortality: 1, 3, 6, 10, 16, 27, 28, 29, 30, 32, 43, 44, 45, 46, 47, 48, 50, 58, 61, 66, 72, 76, 81, 90, 94, 98, 104, 110, 111, 113, 120, 122 and 149.

Test D

For evaluating control of potato leafhopper (*Empoasca fabae* (Harris)) through contact and/or systemic means, the test unit consisted of a small open container with a 5-6-day-old Soleil bean plant (primary leaves emerged) inside. White sand was added to the top of the soil, and one of the primary leaves was excised prior to application of the test compound.

Test compounds were formulated and sprayed at 250 and/or 50 ppm. After spraying of the formulated test compound, the test units were allowed to dry for 1 hour before they were post-infested with 5 potato leafhoppers (18-to-21-day-old adults). A black, screened cap was placed on the top of the test unit, and the test units were held for 6 days in a growth chamber at 20° C. and 70% relative humidity. Each test unit was then visually assessed for insect mortality.

Of the compounds of Formula 1 tested at 250 ppm, the following resulted in at least 80% mortality: 1, 2, 3, 4, 5, 6, 7, 11, 16, 18, 21, 22, 23, 25, 27, 28, 29, 30, 32, 33, 34, 35, 43, 44, 45, 46, 47, 48, 50, 51, 56, 57, 58, 61, 62, 63, 64, 66, 68, 69, 71, 72, 75, 76, 77, 79, 81, 84, 87, 88, 89, 90, 91, 92, 93, 94, 96, 97, 98, 100, 101, 104, 105, 106, 108, 109, 110, 113, 114, 117, 118, 119, 120, 122, 124, 125, 127, 131, 135, 139, 145, 146 and 149.

Of the compounds of Formula 1 tested at 50 ppm, the following resulted in at least 80% mortality: 1, 2, 3, 5, 6, 11, 25, 27, 28, 29, 30, 32, 34, 43, 44, 45, 46, 47, 48, 50, 57, 61, 62, 63, 66, 67, 68, 69, 71, 72, 75, 76, 77, 79, 81, 87, 88, 90, 91, 92, 93, 94, 96, 97, 98, 101, 106, 109, 114, 117, 118, 119, 120, 122, 124, 125, 126, 127 and 139.

Test E

For evaluating control of green peach aphid (*Myzus persicae* (Sulzer)) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds were formulated and sprayed at 250 and/or 50 ppm. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds of Formula 1 tested at 250 ppm, the following resulted in at least 80% mortality: 1, 3, 11, 16, 46, 76, 98, 109, 110, 111, 113, 114, 127 and 149.

Of the compounds of Formula 1 tested at 50 ppm, the following resulted in at least 80% mortality: 3 and 76.

Test F

For evaluating control of cotton melon aphid (*Aphis gossypii* (Glover)) through contact and/or systemic means, the test unit consisted of a small open container with a 5-day-old okra plant inside. This was pre-infested with 30-40 insects on a piece of leaf according to the cut-leaf method, and the soil of the test unit was covered with a layer of sand.

Test compounds were formulated and sprayed at 250 and/or 50 ppm. After spraying, the test units were maintained in a growth chamber for 6 days at 19° C. and 70% relative humidity. Each test unit was then visually assessed for insect mortality.

Of the compounds of Formula 1 tested at 250 ppm, the following resulted in at least 80% mortality: 1, 3, 25, 27, 30, 33, 50, 51, 57, 64, 76, 93, 94, 97, 98, 108, 110, 111, 113, 127, 133 and 135.

Of the compounds of Formula 1 tested at 50 ppm, the following resulted in at least 80% mortality: 1, 3 and 76.

Test G

For evaluating control of the Western Flower Thrips (*Frankliniellla occidentalis* (Pergande)) through contact and/or systemic means, the test unit consisted of a small open container with a 5-7-day-old Soleil bean plant inside.

Test compounds were formulated and sprayed at 250 and/or 50 ppm. After spraying, the test units were allowed to dry for 1 hour, and then about 60 thrips (adults and nymphs) were added to each unit. A black, screened cap was placed on top, and the test units were held for 6 days at 25° C. and 45-55% relative humidity. Each test unit was then visually assessed for plant damage and insect mortality.

Of the compounds of Formula 1 tested at 250 ppm, the following provided very good to excellent levels of control efficacy (30% or less plant damage and/or 100% mortality): 1, 3, 6 and 76.

Of the compounds of Formula 1 tested at 50 ppm, the following provided very good to excellent levels of control efficacy (30% or less plant damage and/or 100% mortality): 1 and 3.

What is claimed is:

1. A compound selected from Formula 1, an N-oxide or salt thereof,

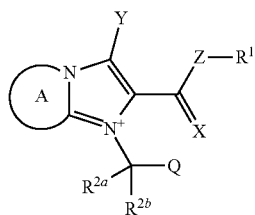

1 wherein the compound of Formula 1 is a compound of Formula 1-1

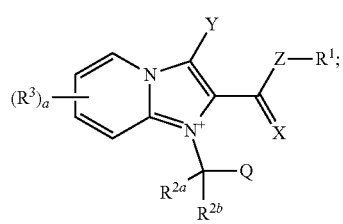

1-1 wherein a is 0, 1, 2 or 3;

X is O or S;

Y is O or S;

Z is a direct bond; or a 1- to 4-atom chain containing chain members selected from carbon atoms and up to 2 heteroatoms independently selected from up to 2 O, up to 2 S, and up to 2 N, wherein up to 2 carbon atom chain members are independently selected from $C(=O)$ and $C(=S)$ and the sulfur atom chain members are independently selected from $S(=O)_n$, each 1- to 4-atom chain being unsubstituted or substituted with up to 4 substituents independently selected from $R^5$, or substituted with up to 9 halogen when $R^5$ is halogen;

$R^1$ is phenyl or pyridinyl, each substituted with 1 to 4 substituents independently selected from $R^4$;

$R^{2a}$ and $R^{2b}$ are independently H, halogen, cyano, $C_1$-$C_3$ alkyl, $C_2$-$C_3$ alkenyl or $C_2$-$C_3$ alkynyl; or $R^{2a}$ and $R^{2b}$ are taken together to form a 3- to 6-membered ring containing ring members selected from carbon atoms and up to one heteroatom selected from O, N and $S(O)_n$;

Q is a 5- or 6-membered heteroaromatic ring, unsubstituted or substituted with up to 3 substituents independently selected from $R^6$;

each $R^3$ is independently halogen, cyano, hydroxy, amino, nitro, $C(=O)OH$, $C(=O)NH_2$, $SO_2NH_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl or $C_2$-$C_6$ haloalkylcarbonyl;

each $R^4$ is independently $C_1$-$C_8$ haloalkylthio, OCN, CHO, $C(=S)NH_2$, $SO_2NH_2$, $C(=O)R^{13}$, $C(=O)OR^{13}$, $NHR^{13}$, $NR^{13}R^{14}$, $C(=O)NR^{16}R^{14}$, $C(=S)NR^{16}R^{14}$, $SO_2NR^{16}R^{14}$, $OC(=O)R^{16}$, $OC(=O)OR^{13}$, $OC(=O)NR^{16}R^{14}$, $N(R^{16})C(=O)OR^{14}$, $N(R^{16})C(=O)NR^{16}R^{17}$, $OSO_2R^{13}$, $OSO_2NR^{16}R^{17}$, $NR^{16}SO_2R^{13}$, $NR^{16}SO_2NR^{16}R^{17}$, $Si(R^{13}R^{14}R^{15})$, $C(=NR^{16})R^{17}$, $C(=NNR^{16}R^{17})R^{18}$, $C(=NN(C(=O)R^{14})R^{16})R^{17}$, $C(=NN(C(=O)OR^{14})R^{16})R^{17}$, $C(=NN(C(=O)NR^{16}R^{17})R^{16})R^{17}$, $C(=NOR^{16})NR^{16}R^{17}$, $ON=CR^{16}R^{17}$, $ONR^{16}R^{17}$, $S(=O)(=NR^{16})R^{17}$, $SO_2NR^{16}C(=O)NR^{17}R^{18}$, $P(=X^2)R^{13}R^{14}$, $OP(=X^2)R^{13}R^{14}$, $OP(=X^2)(OR^{13})R^{14}$, $OP(=X^2)(OR^{13})OR^{14}$, $N=CR^{16}R^{17}$, $NR^{16}N=CR^{17}R^{18}$, $NR^{16}NR^{17}R^{18}$, $NR^{16}C(=X^2)NR^{17}R^{18}$, $NR^{16}C(=NR^{16})NR^{17}R^{18}$, $NR^{16}NR^{16}C(=X^2)NR^{17}R^{18}$ or $NR^{16}NR^{16}SO_2NR^{17}R^{18}$, or each $R^4$ is independently $C_4$-$C_{10}$ alkylcycloalkyl, $C_6$-$C_{14}$ cycloalkylcycloalkyl, $C_5$-$C_{10}$ alkylcycloalkylalkyl, $C_3$-$C_8$ cycloalkenyl, $C_3$-$C_8$ cycloalkoxy, $C_4$-$C_{10}$ cycloalkylalkoxy, $C_3$-$C_{10}$ cycloalkoxyalkyl, $C_3$-$C_{10}$ cycloalkoxyalkoxy, $C_2$-$C_8$ alkenyloxy, $C_2$-$C_8$ alkynyloxy, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{12}$; or each $R^4$ is independently $Z^1Q^1$;

each $R^5$ is independently halogen, cyano, nitro, $C_1$-$C_3$ alkyl, $C_1$-$C_3$ haloalkyl, $C_2$-$C_3$ alkenyl, $C_2$-$C_3$ haloalkenyl, $C_2$-$C_3$ alkynyl, $C(=O)OR^8$, $C(=O)NR^9R^{10}$ or $Z^1Q^2$;

each $R^6$ is independently halogen, cyano, nitro, CHO, $C(=O)OH$, $C(=O)NH_2$, $C(=O)R^7$, $C(=O)OR^8$, $C(=O)NR^9R^{10}$, $OR^8$, $S(O)_nR^7$, $SO_2NR^9R^{10}$ or $Si(R^7)_3$; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, $C_2$-$C_6$ alkylcarbonyl or $C_2$-$C_6$ alkoxycarbonyl, each unsubstituted or substituted with at least one substituent independently selected from the group consisting of halogen, cyano, nitro, CHO, $C(=O)OH$, $C(=O)NH_2$, $C(=O)R^7$, $C(=O)OR^8$, $C(=O)NR^9R^{10}$, $OR^8$, $S(O)_nR^7$, $SO_2NR^9R^{10}$ and $Si(R^7)_3$;

each $R^7$, $R^8$, $R^9$ and $R^{10}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $Z^1$ is independently a 1- to 4-atom chain containing chain members selected from carbon atoms and 1 to 2 heteroatoms independently selected from up to 2 O, up to 2 S, and up to 2 N, wherein up to 2 carbon atom chain members are independently selected from $C(=O)$ and $C(=S)$ and the sulfur atom chain members are independently selected from $S(=O)_n$, each 1- to 4-atom chain being unsubstituted or substituted with up to 4 substituents independently selected from $R^5$, or substituted with up to 9 halogen when $R^5$ is halogen;

each $X^2$ is independently O or S;

each $Q^1$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_n(=NR^{19})_z$, each ring or ring system optionally substituted with up to 4 substituents independently selected from the group consisting of halogen, cyano, nitro, CHO, $C(=O)OH$, $C(=O)NH_2$, $C(=O)R^7$, $C(=O)OR^8$, $C(=O)NR^9R^{10}$, $OR^8$, $S(O)_nR^7$, $SO_2NR^9R^{10}$, $Si(R^7)_3$ and $R^{11}$;

each $Q^2$ is independently phenyl or a 5- or 6-membered heteroaromatic ring, each unsubstituted or substituted with up to 3 substituents independently selected from the group consisting of halogen, cyano, nitro, CHO, $C(=O)OH$, $C(=O)NH_2$, $C(=O)R^7$, $C(=O)OR^8$, $C(=O)NR^9R^{10}$, $OR^8$, $S(O)_nR^7$, $SO_2NR^9R^{10}$, $Si(R^7)_3$ and $R^{11}$;

each $R^{11}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $R^{12}$ is independently halogen, cyano, nitro, CHO, $C(=O)OH$, $C(=O)NH_2$, $C(=O)R^7$, $C(=O)OR^8$, $(=O)NR^9R^{10}$, $OR^8$, $S(O)_nR^7$, $SO_2NR^9R^{10}$, $Si(R^7)_3$ or $Z^1Q^2$;

each $R^{13}$, $R^{14}$ and $R^{15}$ is independently $C_2$-$C_6$ alkynyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{12}$; or $Q^2$;

each $R^{16}$, $R^{17}$ and $R^{18}$ is independently H, $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{12}$; or $Q^2$;

each $R^{19}$ is independently H, cyano, OCN, SCN, CHO, $C(=O)OH$, $C(=O)NH_2$, $C(=S)NH_2$, $SO_2NH_2$, $C(=O)R^{13}$, $C(=O)OR^{13}$, $NHR^{13}$, $NR^{13}R^{14}$, $C(=O)$ $NR^{16}R^{14}$, $C(=S)NR^{16}R^{14}$, $SO_2NR^{16}R^{14}$, $OC(=O)R^{16}$, $OC(=O)OR^{13}$, $OC(=O)NR^{16}R^{14}$, $N(R^{16})C(=O)R^{16}$, $N(R^{16})C(=O)OR^{14}$, $N(R^{16})C(=O)NR^{16}R^{17}$, $OSO_2R^{13}$, $OSO_2NR^{16}R^{17}$, $NR^{16}SO_2R^{13}$, $NR^{16}SO_2NR^{16}R^{17}$, $Si(R^{13}R^{14}R^{15})$ or $Z^1Q^2$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{12}$;

each n is independently 0, 1 or 2; and u and z in each instance of $S(=O)_u(=NR^{19})_z$ are independently 0, 1 or 2, provided that the sum of u and z in each instance of $S(=O)_u(=NR^{19})_z$ is 0, 1 or 2.

2. The compound of claim 1 wherein
X and Y are O;
$R^{2a}$ and $R^{2b}$ are H.

3. The compound of claim 2 wherein Z is a direct bond.

4. The compound of claim 3 wherein Q is

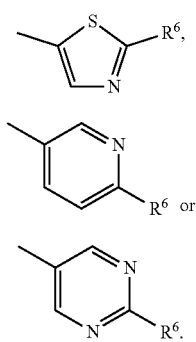

5. The compound of claim 4 wherein
$R^1$ is phenyl, substituted with 1 to 4 substituents independently selected from $R^4$;
$R^3$ is F, Cl or $CH_3$;
a is 0 or 1; and
$R^6$ is H, F, Cl, Br, $CH_3$, $CHF_2$ or $CF_3$.

6. A composition comprising a compound of claim 1 and at least one additional component selected from the group consisting of surfactants, solid diluents and liquid diluents, said composition optionally further comprising at least one additional biologically active compound or agent.

7. The composition of claim 6 wherein the at least one additional biologically active compound or agent is selected from the group consisting of abamectin, acephate, acequinocyl, acetamiprid, acrinathrin, afidopyropen, amidoflumet, amitraz, avermectin, azadirachtin, azinphos-methyl, benfuracarb, bensultap, bifenthrin, bifenazate, bistrifluron, borate, buprofezin, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyclaniliprole, cycloprothrin, cycloxaprid, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin, flonicamid, flubendiamide, flucythrinate, flufenerim, flufenoxuron, flufenoxystrobin, flufensulfone, fluorpyram, flupiprole, flupyradifurone, fluvalinate, tau-fluvalinate, fonophos, formetanate, fosthiazate, halofenozide, heptafluthrin, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiodicarb, methomyl, methoprene, methoxychlor, metofluthrin, monocrotophos, monofluthrin, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide, pymetrozine, pyrafluprole, pyrethrin, pyridaben, pyridalyl, pyrifluquinazon, pyriminostrobin, pyriprole, pyriproxyfen, rotenone, ryanodine, silafluofen, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultap-sodium, tolfenpyrad, tralomethrin, triazamate, trichlorfon, triflumuron, all strains of *Bacillus thuringiensis*, entomopathogenic bacteria, all strains of *Nucleo polyhedrosis* viruses, entomopathogenic viruses and entomopathogenic fungi.

8. The composition of claim 7 wherein the at least one additional biologically active compound or agent is selected from the group consisting of abamectin, acetamiprid, acrinathrin, afidopyropen, amitraz, avermectin, azadirachtin, benfuracarb, bensultap, bifenthrin, buprofezin, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, lambda-cyhalothrin, gamma- cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, flufensulfone, flupiprole, flupyradifurone, fluvalinate, formetanate, fosthiazate, heptafluthrin, hexaflumuron, hydramethylnon, imidacloprid, indoxacarb, lufenuron, meperfluthirn, metaflumizone, methiodicarb, methomyl, methoprene, methoxyfenozide, metofluthrin, monofluthrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, tetramethylfluthrin, triazamate, triflumuron, all strains of *Bacillus thuringiensis* and all strains of *Nucleo polyhedrosis* viruses.

9. A method for controlling an invertebrate pest comprising contacting the invertebrate pest or its environment with a biologically effective amount of a compound of claim 1.

10. A treated seed comprising a compound of claim 1 in an amount of from about 0.0001 to 1% by weight of the seed before treatment.

\* \* \* \* \*